United States Patent
Grunden et al.

(10) Patent No.: US 12,350,185 B2
(45) Date of Patent: Jul. 8, 2025

(54) ORTHOSIS FOR FIXING A SHOULDER JOINT

(71) Applicant: BSN medical GmbH, Hamburg (DE)

(72) Inventors: Jennifer Grunden, Hamburg (DE); Timo Schmeltzpfennig, Buchholz (DE); Joachim Bauer, Hamburg (DE)

(73) Assignee: BSN MEDICAL GMBH, Hamburg (DE)

( * ) Notice: Subject to any disclaimer, the term of this patent is extended or adjusted under 35 U.S.C. 154(b) by 1032 days.

(21) Appl. No.: 14/397,348

(22) PCT Filed: Apr. 29, 2013

(86) PCT No.: PCT/EP2013/058932
§ 371 (c)(1),
(2) Date: Feb. 3, 2015

(87) PCT Pub. No.: WO2013/160487
PCT Pub. Date: Oct. 31, 2013

(65) Prior Publication Data
US 2015/0157488 A1    Jun. 11, 2015

Related U.S. Application Data

(60) Provisional application No. 61/639,422, filed on Apr. 27, 2012.

(30) Foreign Application Priority Data

Apr. 27, 2012 (DE) .................. 10 2012 009 107.9
Apr. 17, 2013 (EP) ....................................... 13164211

(51) Int. Cl.
*A61F 5/37*    (2006.01)
*A44B 11/25*    (2006.01)
(Continued)

(52) U.S. Cl.
CPC ........ *A61F 5/3723* (2013.01); *A44B 11/2592* (2013.01); *A44B 11/28* (2013.01);
(Continued)

(58) Field of Classification Search
CPC ........ A61F 5/37; A61F 5/3738; A61F 5/3723; A61F 5/373; A61F 5/3761; A61F 5/0102;
(Continued)

(56) References Cited

U.S. PATENT DOCUMENTS 868,298 A * 10/1907 Siner ...................... A41F 1/00
                                                          24/702
1,188,709 A    6/1916 Wenzel
(Continued)

FOREIGN PATENT DOCUMENTS

CH    694612 A5    4/2005
DE    188606 C    7/1906
(Continued)

OTHER PUBLICATIONS

WO 2005120404 A1—English Translation; Gazielly, Dominique (Jul. 2001).*
(Continued)

*Primary Examiner* — Michelle J Lee
(74) *Attorney, Agent, or Firm* — Shumaker, Loop & Kendrick, LLP; S. Alexander Long, Jr.

(57) ABSTRACT

An orthosis having a strap arrangement which is designed to engage on an arm section at the elbow or adjacent to the elbow of the arm extending from the first shoulder joint, which is to be immobilized, in order to fix the elbow frontally on the body of the patient. The strap arrangement has a first strap section which is provided for at least partially looping around the arm section. The strap arrangement has a second strap section which is provided for at least partially looping around the arm section, and is incorporated (Continued)

into the strap arrangement such that, in the fitted state of the orthosis, the second strap section exerts on the arm section a second force which has at least a second component running parallel to the sagittal plane of the patient and horizontally.

7 Claims, 13 Drawing Sheets

(51) Int. Cl.
  *A44B 11/28* (2006.01)
  *A61F 5/01* (2006.01)
(52) U.S. Cl.
  CPC ............... *A61F 5/01* (2013.01); *A61F 5/373* (2013.01); *A61F 5/3738* (2013.01)
(58) Field of Classification Search
  CPC ............ A61F 5/04; A61F 5/3715–3753; A61F 5/01–0104; A61F 5/0118; A61F 5/013; A44B 11/25; A44B 11/28; A44B 11/2584; A44B 11/2588; A44B 11/2596; A44B 11/26; A44B 11/263; A44B 11/266; A44B 11/00; A44B 11/258–2592; A44B 11/2503; A61H 1/0274; A61H 1/0277; A61H 1/0281; A61H 2201/1614; A61H 2201/1616; A61H 2201/1635; A61H 2201/1638
  USPC ........ 602/4, 5, 19, 20, 61, 62; 128/878, 869, 128/875, 876, 874, 825, DIG. 19, 128/DIG. 15; 5/621, 623; 2/16
  See application file for complete search history.

(56) References Cited

U.S. PATENT DOCUMENTS

| | | | | |
|---|---|---|---|---|
| 1,808,422 A | * | 6/1931 | MacDonald | A61F 5/05808 602/4 |
| 2,344,844 A | * | 3/1944 | Baldeschwieler | A61F 5/3746 602/4 |
| 4,198,964 A | * | 4/1980 | Honneffer | A61F 5/05808 128/DIG. 19 |
| 4,372,301 A | * | 2/1983 | Hubbard | A61F 5/3738 24/265 R |
| 4,550,724 A | * | 11/1985 | Berrehail | A61F 5/3746 128/874 |
| 4,878,490 A | * | 11/1989 | Scott | A61F 5/3746 602/20 |
| 5,334,132 A | * | 8/1994 | Burkhead | A61F 5/3738 602/4 |
| 5,393,300 A | * | 2/1995 | Bauerfeind | A61F 13/146 128/876 |
| 5,772,617 A | * | 6/1998 | Lay | A61F 5/3738 128/878 |
| 5,830,165 A | * | 11/1998 | Rowe | A61F 5/3738 128/876 |
| 6,146,346 A | | 11/2000 | Godwin | |
| 2003/0176823 A1 | | 9/2003 | Mason | |
| 2003/0187373 A1 | * | 10/2003 | Gaylord | A61F 5/3753 602/4 |
| 2004/0215119 A1 | * | 10/2004 | Avon | A61F 5/3738 602/4 |
| 2005/0187504 A1 | | 8/2005 | Modglin | |
| 2006/0258966 A1 | * | 11/2006 | Hargrave | A61F 5/3753 602/20 |
| 2007/0016121 A1 | | 1/2007 | Kaminski et al. | |
| 2012/0209159 A1 | * | 8/2012 | Fout | A61F 5/3738 602/4 |

FOREIGN PATENT DOCUMENTS

| | | | | |
|---|---|---|---|---|
| DE | 4029622 C1 | * | 3/1992 | ........... A61F 5/3738 |
| DE | 4210692 C1 | * | 4/1993 | ........... A61F 5/3753 |
| DE | 4314785 C1 | | 6/1994 | |
| DE | 19745705 C1 | | 2/1999 | |
| DE | 20116743 | | 1/2002 | |
| DE | 102004028604 A1 | | 12/2005 | |
| DE | 112011100230 | | 10/2012 | |
| WO | WO 2005120404 A1 | * | 12/2005 | ........... A61F 5/3738 |
| WO | WO 2011086315 A1 | * | 7/2011 | ........... A61F 5/3738 |

OTHER PUBLICATIONS

International Search Report for PCT/EP2013/058932 dated Jul. 23, 2013.
Search Report for EP1316421 dated Jul. 10, 2013.

* cited by examiner

ORTHOSIS FOR FIXING A SHOULDER JOINT

TECHNICAL FIELD AND BACKGROUND OF THE INVENTION

The present invention relates to an orthosis for immobilizing a shoulder joint of a patient.

In the case of shoulder joint injuries, it is often necessary for this joint to be immobilized or fixed by means of an orthosis. Such an orthosis is known for example from DE 197 45 705 C1. In particular, such an orthosis should prevent an excessive abduction of the upper arm, that is to say a sideward splaying of the arm, and an anteversion and a retroversion of the upper arm, that is to say pivoting forward and rearward.

In the case of the orthosis known from the prior art, proceeding from the injured shoulder, two straps run anteriorly and posteriorly from said shoulder in the direction of the elbow of the arm extending from the injured shoulder joint. Attached to the free end of said two straps is a lower arm support which receives the lower arm. Furthermore, from the starting point of the two straps running over the upper arm, there extends a shoulder strap which runs posteriorly to the contralateral shoulder and from there anteriorly downward in order to hold the wrist of the arm extending from the injured shoulder. Finally, a circular strap is provided which is secured by way of a first end to the arm of the injured shoulder joint at an arm section thereof at or adjacent to the elbow, and which leads posteriorly around the patient to the wrist region of the lower arm support. This orthosis known from the prior art however gives rise to two problems.

Firstly, the position of the upper arm extending from the injured shoulder joint is only inadequately fixed by the orthosis. An abduction and an anteversion and retroversion remain possible as before, albeit to a restricted extent.

Furthermore, it has proven to be extremely difficult for the patient to fit such an orthosis on their own because, after the orthosis has been fitted to the arm extending from the injured shoulder, the circular strap still has to be led from the corresponding wrist, over the back and to the upper arm again, and fixed there. It is thus necessary for the circular strap to be laid posteriorly around the body without using the arm of the first shoulder, which is particularly difficult and cannot be performed by the patient themselves.

SUMMARY OF THE INVENTION

Taking the prior art as a starting point, it is therefore the object of the present invention to provide an orthosis for immobilizing a shoulder joint, which orthosis reliably fixes the shoulder joint, that is to say prevents an abduction and an anteversion or retroversion of the corresponding arm from the fixed position to the side of the body.

Said object is achieved by means of an orthosis having a strap arrangement which is designed to engage on an arm section at the elbow or adjacent to the elbow of the arm extending from the first shoulder joint, which is to be immobilized, in order to fix the elbow frontally on the body of the patient, wherein the strap arrangement has a first strap section which is provided for at least partially looping around the arm section, wherein the first strap section is incorporated into the strap arrangement such that, in the fitted state of the orthosis, the first strap section exerts on the arm section a first force which has at least a first component running parallel to the frontal plane of the patient and horizontally, wherein the first component points from the arm section toward the body, such that the first force has an adductive effect on the arm, wherein the strap arrangement has a second strap section which is provided for at least partially looping around the arm section, and wherein the second strap section is incorporated into the strap arrangement such that, in the fitted state of the orthosis, the second strap section exerts on the arm section a second force which has at least a second component running parallel to the sagittal plane of the patient and horizontally.

Accordingly, in the case of the orthosis according to the invention, a first strap section and a second strap section are provided which engage on the arm extending from the injured shoulder, in the region of an arm section extending around the elbow, in such a way as to at least partially loop around said arm. They should at least partially loop around at least to such an extent that the strap sections in question are capable, under the action of tension in their direction of extent, of imparting a force to the arm section. Within the context of the invention, the expression "arm section" means in this case that region of the arm in question which comprises the elbow itself and the regions adjacent thereto.

In the fitted state of the orthosis, in which the arm extending from the injured shoulder lies frontally against the body, the first strap section exerts on the arm section a force which is directed toward the body and which preferably run substantially parallel to the frontal plane of the patient but which has at least a first component running horizontally and parallel to the frontal plane. In this way, the arm section is pulled against the body owing to the first strap section.

At the same time, the second strap section exerts on the arm section a second force which has at least a component running horizontally and parallel to the sagittal plane and thus perpendicular to the first component. Said second force preferably runs substantially parallel to the sagittal plane. Said second component preferably has a retroverting action on the arm in question.

By contrast to the prior art, in which only a single force is exerted on the arm section, two mutually perpendicular force components act on the arm section, such that in the case of the orthosis according to the invention, it is achieved that the arm section and thus the arm extending from the injured shoulder are reliably prevented from performing an abduction and a retroversion or anteversion. In particular, the elbow is fixed laterally to the body of the patient in the frontal plane in a vertical profile with respect to the shoulder joint that is to be immobilized.

In a preferred embodiment, the first strap section is provided so as to run anteriorly along the body of the patient away from the arm section, and the second component is directed toward the posterior, such that the second force effects a retroversion of the first arm. Said retroversion however counteracts the first force, such that the upper arm is altogether pulled against the body and fixed. Here, it is furthermore preferable if the first strap section forms the first end of a circular strap which is designed to run circularly and horizontally around the patient, wherein the second end of the circular strap engages on the arm section.

Here, it is possible firstly for the second end, which is remote from the first end of the circular strap and thus from the first strap section, to be connected to the first end, wherein the second strap section is then formed on a first end of a shoulder strap of the strap arrangement, which shoulder strap is designed to run posteriorly from the arm section to the contralateral shoulder of the patient in relation to the first shoulder and anteriorly from the contralateral shoulder to the circular strap, and wherein the second end, which is remote from the first end of the shoulder strap, is connected to the circular strap at a first connecting point on the anterior side of the patient. The first force is then imparted by the circular strap, which is in the form of a closed ring, whereas the tension on the shoulder strap effects the second force.

In this case, the additional advantage is attained that, owing to the connection of the second end of the shoulder strap to the circular strap, a loop formed from circular strap and shoulder strap is created, wherein the patient, after fitting the arm section, need merely place the contralateral shoulder in relation to the injured shoulder into said loop, such that the process of fitting the orthosis is greatly simplified.

Furthermore, it is also possible for the second strap section to be provided on a second end, which is remote from the first end, of the circular strap, wherein the strap arrangement then also has a shoulder strap which is connected to the circular strap at a first connecting point, which is situated on the anterior side of the body of the patient, and at a second connecting point, which is situated on the posterior side of the body of the patient.

In this exemplary embodiment, both the first force and also the second force are exerted on the arm section by the ends of the circular strap. In this case, the shoulder strap running over the contralateral shoulder does not exert a force on the arm section. However, in this case, too, there is the advantage that the shoulder strap and the circular strap together form a loop into which the patient can simply place the contralateral shoulder in order to fit the orthosis.

Furthermore, in both alternatives, the shoulder strap ensures that the circular strap is held in its horizontal position and cannot slip downward on the patient.

In the embodiments described above, it is preferably provided that the first and the second connecting point at which the circular strap and the shoulder strap are connected to one another are displaceable along the circular strap. Furthermore, the first connecting point may also be displaceable along the shoulder strap. Altogether, it is then firstly possible for the orthosis to be adapted in a simple manner to different patient sizes, and secondly, the magnitude of the first and second forces can also be adjusted by displacing the connecting points.

Furthermore, the orthosis according to the invention may have a fastener device which has an open and a closed position, wherein the strap arrangement is designed such that, in the closed position, the first force and the second force are exerted on the arm section, and that, in the open position, neither the first force nor the second force act on the arm section.

If the strap arrangement is dimensioned so as to bear adequately tightly against the body of the patient in the closed position of the fastener device, the fastener device has the great advantage for the patient that, simply by releasing said fastener device, that is to say transferring said fastener device from the closed position into the open position, the action of both forces is eliminated, such that the arm extending from the injured shoulder is immediately released. Conversely, the action of both forces can be immediately obtained simply by closing the fastener device. This simplifies the fitting process considerably.

It is furthermore pointed out that an independently inventive concept is that of using, in the case of an orthosis with a strap arrangement, a fastener device which is designed such that, in its closed position, both a first and a second force are exerted on the body, and in particular only on one body section, of the patient, whereas in the open position, both forces are eliminated, and that the use of said concept is not restricted to orthoses for fixing a shoulder joint but may be used in numerous other orthoses.

In the case of the shoulder orthosis according to the invention, said fastener device may preferably be provided at the first connecting point at which the shoulder strap and the circular strap are connected to one another and which, in the fitted state of the orthosis, is situated on the anterior side of the body of the patient. The fastener device is thus easily accessible for the patient and, after the contralateral shoulder in relation to the injured shoulder has been placed in, can be transferred from the open position into the closed position such that both forces then act on the arm section.

The circular strap preferably has an anterior section, which extends from the first connecting point to the first end of the circular strap, and a posterior section, which is provided so as to run horizontally and posteriorly around the body of the patient, which posterior section extends from a posterior section end to the second end of the circular strap, and on which posterior section the first connecting point is arranged. The anterior section and the posterior section may be detachably connected to one another. The fastener device may then preferably be designed such that, in the closed position of the fastener device, the anterior section and the posterior section are connected to one another, and that, in the open position, the anterior section and the posterior section are detached from one another. In this way, the circular strap can be disconnected on the anterior side of the body of the patient, such that the orthosis can be fitted in a simple manner. It is advantageous here for the fastener device to be designed such that the shoulder strap is connected to the posterior section in the open position and in the closed position. Then, even in the open position, the loop formed from the shoulder strap and a posterior part of the circular strap is maintained, which is advantageous for the fitting process.

To enable the circular strap to be tightened, the fastener device has a fixing device for fixing the first connecting point along the posterior section, wherein the fixing device is designed such that the first connecting point can be displaced toward the second end of the circular strap by pulling on the posterior section end, whereas a movement of the first connecting point towards the posterior section end as a result of a pulling action on the second end of the circular strap is blocked.

To make it possible for the lower arm of the arm extending from the injured shoulder to likewise be held in a defined position, the orthosis preferably has a holding device which is designed to hold the lower arm in its flexed position. Here, the holding device may have a holding strap which is connected by way of a first end to the strap arrangement and which is designed to hold the lower arm of the arm extending from the first shoulder joint in the region of the wrist thereof. To transfer the load of the lower arm to the strap arrangement, the holding strap may be connected by way of a first end to the shoulder strap, or the first end of said holding strap is formed by the shoulder strap. In particular, the holding strap may be designed to loop around the lower arm, wherein a second end of the holding strap can be detachably connected to the shoulder strap.

Finally, the orthosis according to the invention may have a lower arm support which is designed to receive the lower arm and the hand of the arm extending from the first shoulder joint. The hand is thus prevented from bending downward when the orthosis is worn, which can lead to damage.

In an independently inventive aspect, a bandage according to the invention has a fastener with a first fastener part and a second fastener part that can be detachably connected to one another, wherein the first and the second fastener part have connecting devices for straps of the strap arrangement, wherein the first fastener part has a stud, wherein the second fastener part has an attachment end, at which the connecting device is formed, and a coupling end, and between the attachment end and the coupling end, there is provided a guide track which extends in a fastener plane from an entry opening to a guide track end and which is designed to receive the stud and guide it between the entry opening and the guide track end along the guide track, wherein the stud has a first section close to the connecting device of the first fastener part and a second section which adjoins the first section and which is arranged at that end of the first section which is situated opposite the connecting device, wherein the dimension of the first section perpendicular to the direction of extent of the stud corresponds to the dimension of the guide track in the fastener plane at the guide track end, and wherein the dimension of the second section perpendicular to the direction of extent of the stud is greater than the dimension of the guide track at the guide track end, such that the second section restricts a movement of the stud relative to the second fastener part perpendicular to the fastener plane when the stud is at the guide track end.

A fastener constructed in this way can, even in a fitted state of an orthosis with a strap arrangement, be easily closed by the patient because the patient merely has to insert the stud into the guide track in the region of the entry opening, and the stud, when it has been moved along the guide track to the guide track end, is then prevented from being released from the guide track, that is to say the two ends, which are to be connected, of the strap arrangement are locked together. Since the dimensions of the second section of the stud perpendicular to the direction of extent thereof are greater than the dimensions of the guide track at the guide track end, a movement of the stud perpendicular to the plane of the guide track is prevented regardless of the position of the stud relative to the guide track end.

In a preferred embodiment of the fastener, the guide track is designed such that either any possible movement of the stud out of its position in the guide track end runs perpendicular to a connecting line between the attachment end and the coupling end, or the projection of said movement onto the connecting line points toward the attachment end. This embodiment has the effect that the stud is held at the guide track end under the action of a tension being exerted on the fastener by a strap arrangement of an orthosis.

Accordingly, if a fastener constructed in this way is used in particular in an orthosis according to the invention, which in the closed state is under a certain preload which then leads to a force being exerted on the fastener along the connecting line between the attachment end and the coupling end, the following advantage is attained. When closing the orthosis, it is merely necessary for the stud to be inserted into the correspondingly dimensioned entry opening of the guide track and moved along the guide track to the guide track end, wherein said movement is predefined simply by the shape of the guide track and is facilitated by the force described above.

This is because, when the stud is spaced apart from the guide track end, the first fastener part is subjected to said force, which pulls the stud toward the guide track end. Conversely, the stud must be moved away from the guide track end counter to said force if it is intended to open the orthosis. This is the case even if the movement out of the guide track end runs perpendicular to the connecting line, because then, there are at least friction forces acting which must be overcome in the event of a movement out of the guide track end. The fastener according to the invention thus locks in the presence of a preload in the strap arrangement itself.

In a further preferred embodiment of the fastener, the guide track end and the stud are designed such that the first fastener part is pivotable relative to the second fastener part when the stud is situated at the guide track end. This makes it possible for the two parts of the fastener to be oriented relative to one another in accordance with the forces acting thereon. Here, it is possible in particular for the first section to have a circular cross section and for the diameter of the first section to correspond to the width of the guide track end, preferably of the entire guide track. In this context, the expression "width" is to be understood to mean the dimension of the guide track perpendicular to the profile thereof or perpendicular to the respective tangent. If the width of the entire guide track, if appropriate with the exception of a section with a detent projection, corresponds to the diameter of the stud, said stud is guided over the entire length of the guide track but can be pivoted and thus oriented with respect to the acting.

Furthermore, in the case of the fastener, it is advantageous for locking means to be provided in order to hold the stud in the guide track, preferably at the guide track end. In particular, the locking means may be designed by virtue of a detent projection being formed in the guide track such that the width of the guide track is reduced in the region of the detent projection, wherein the second fastener part is designed such that the first section of the stud, during the movement from the entry opening to the guide track end and vice versa, must be moved past the detent projection counter to an elastic opposing force. This prevents the stud from being able to move out of the guide track, or even away from the guide track end toward the entry opening, without a force having to be exerted either on the stud itself or on a part of the second fastener part. The stud is thus also mechanically locked in its position at the guide track end.

The second fastener part advantageously has a further connecting device for a further strap. It is thus possible for multiple straps of the strap arrangement of the orthosis to converge at the second connecting part.

It is furthermore preferable if, adjacent to the guide track in the region of the guide track end, preferably adjacent to the entire guide track, an abutment section of uniform thickness is provided, wherein the first section of the stud has, in its axial direction, a length corresponding to the thickness of the abutment section. In this case, the second fastener part is guided between the projections on the stud, and the movement of the stud along the guide track runs exclusively in the plane of the planar section. This permits a simple fastening movement which can be easily performed even by a patient with restricted mobility.

Furthermore, the guide track may extend to the edge of the second fastener part, wherein the entry opening is formed in the edge of the second fastener part. It is then possible for the first fastener part to be connected to the second in such a way that the fastening movement takes place exclusively in the plane of the second fastener part, that is to say the second fastener part is pulled, in the manner of a hook, over the stud.

Here, it is preferable for the entry opening to be provided, between the attachment end and the coupling end, on a first side of the connecting line between the attachment ends, wherein the further connecting device is provided on a second side, situated opposite the first side, of the connecting line. In this way, the two fastener parts can be brought into engagement with one another by means of a movement in the plane of the planar section, without a strap that is attached to the further connecting device posing an obstruction.

Furthermore, in the case of such a design, it is preferable for the projection of the entry opening on to the connecting line between the attachment end and the coupling end to be situated further remote from the coupling end than the projection of the guide track onto the connecting line. It is ensured in this way that the stud is pulled toward the guide track end, and thus away from the entry opening, under the action of the preload in the strap arrangement.

The guide track preferably runs with a uniform direction of curvature from the entry opening to the guide track end, which permits simple fastening of the fastener. Here, if the guide track is designed, at the guide track end, such that the movement of the stud out of the position at the guide track end runs parallel to the connecting line between the connecting end and the coupling end, it is ensured that the stud remains reliably at the guide track end under the action of the preload.

Finally, in one preferred embodiment, the stud of the first closure part may be designed so as to have a free end which is provided with a depression running in the axial direction of the stud. In this way, the patient, by placing a finger into the depression, can hold the stud in its position or move the stud while using the same hand to guide the second fastener part onto the stud. It is thus possible for the fastener to be fastened using one hand.

BRIEF DESCRIPTION OF THE DRAWINGS

The present invention will be explained below with reference to a drawing which shows merely preferred exemplary embodiments of orthoses according to the invention, wherein.

DETAILED DESCRIPTION OF THE INVENTION

Figure 4:
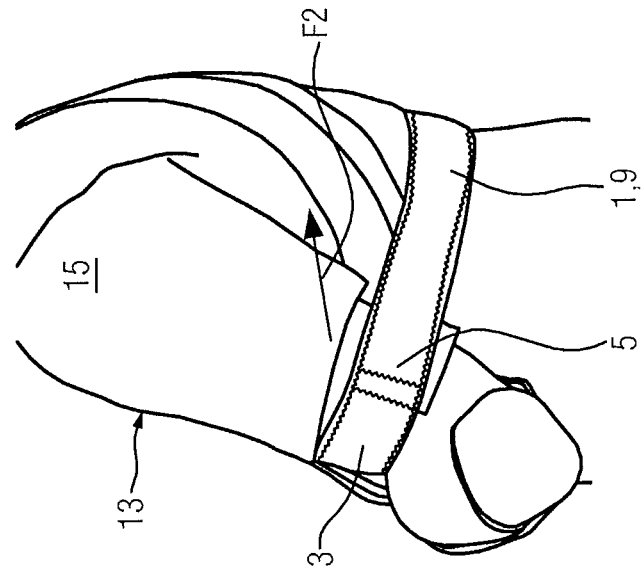
FIG. 4 shows the lateral part of the first exemplary embodiment in the fitted state.

As can be seen from FIGS. 1 to 6, the first exemplary embodiment of an orthosis according to the invention for immobilizing a shoulder joint has a strap arrangement with a circular strap 1 which has a first and a second end 3, 5 (see FIG. 4). The circular strap 1 is made up of an anterior section 7, which extends from the first end 3 and runs anteriorly over the patient, and a posterior section 9, which runs posteriorly and horizontally around the patient from the second end 5. Here, in this exemplary embodiment, the first and the second end 3, 5 of the circular strap 1 are connected to one another or merge into one another. In this exemplary embodiment, the first end 3 of the circular strap 1 forms a first strap section which partially loops around an arm section 11 of that arm 13 of the patient which extends from the first shoulder joint 15, which is to be immobilized.

Here, the expression "arm section" refers to that region of the arm 13 extending from the injured first shoulder joint 15 which encompasses the elbow itself and the regions adjacent thereto.

Figure 1:
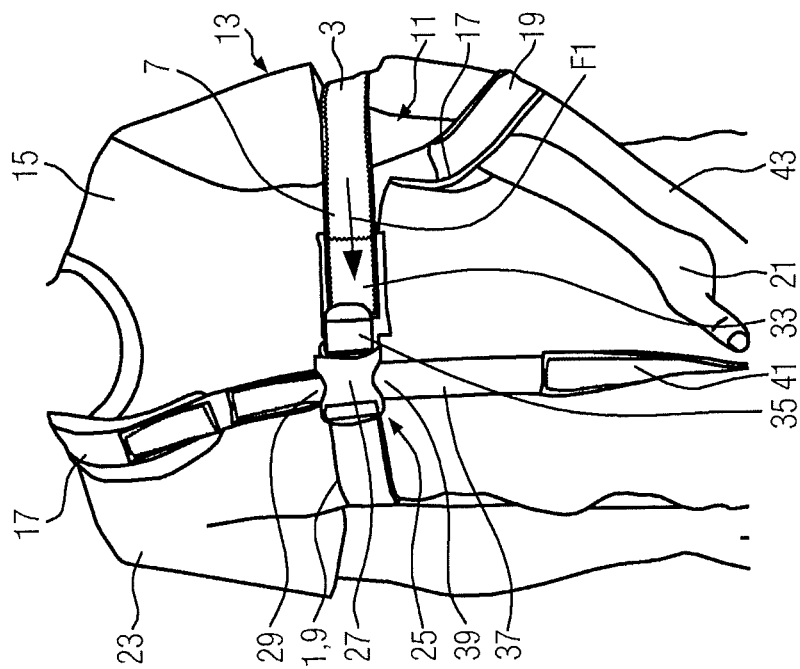
FIG. 1 shows the anterior part of a first exemplary embodiment of an orthosis in the fitted and non-closed state.
Figure 2:
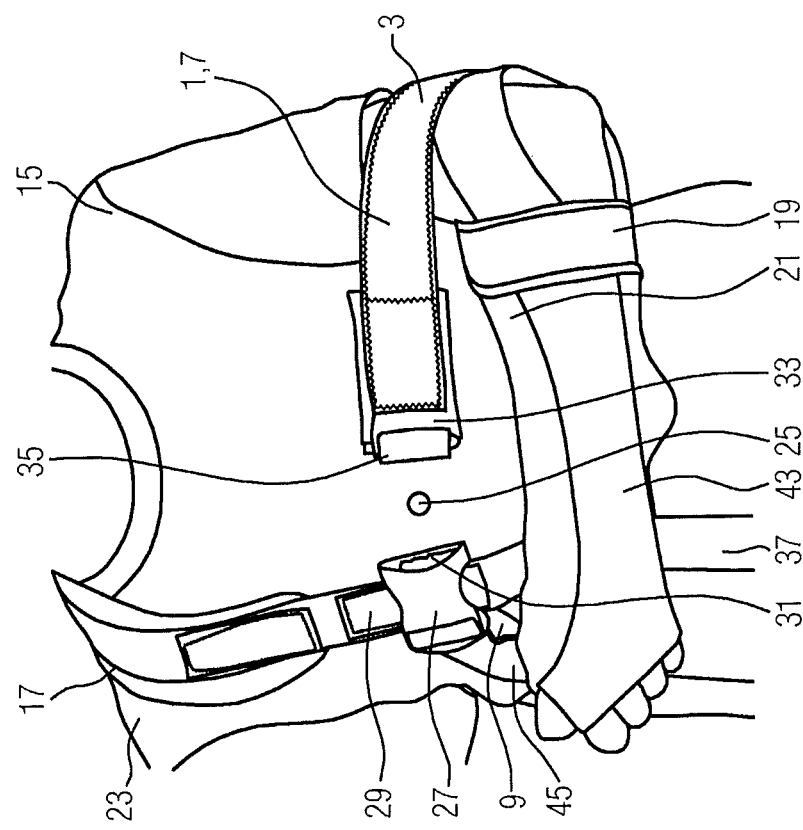
FIG. 2 shows the anterior part of a first exemplary embodiment of an orthosis in the fitted and closed state.
Figure 3:
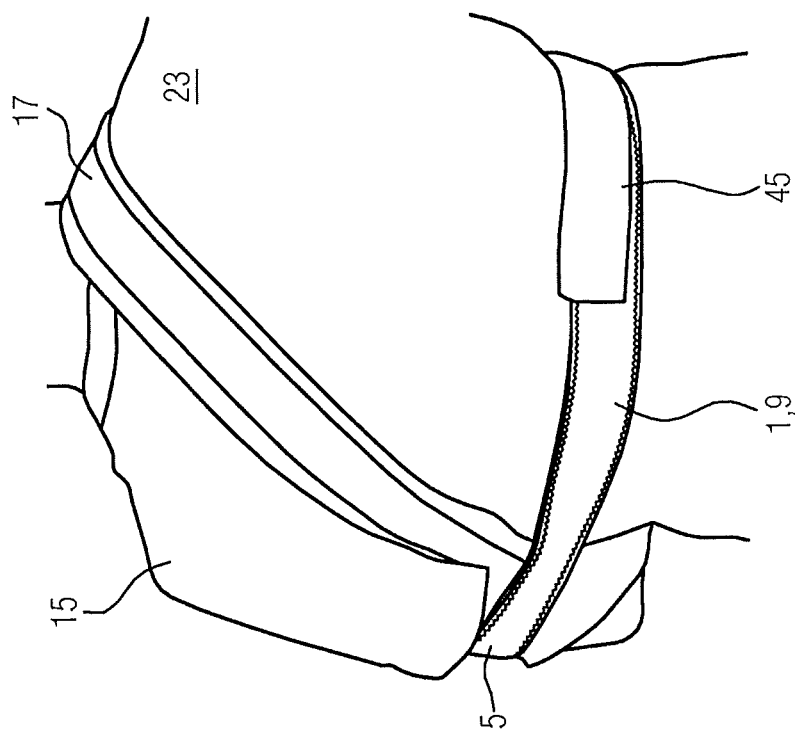
FIG. 3 shows the posterior part of the first exemplary embodiment in the fitted state.
Figure 5:
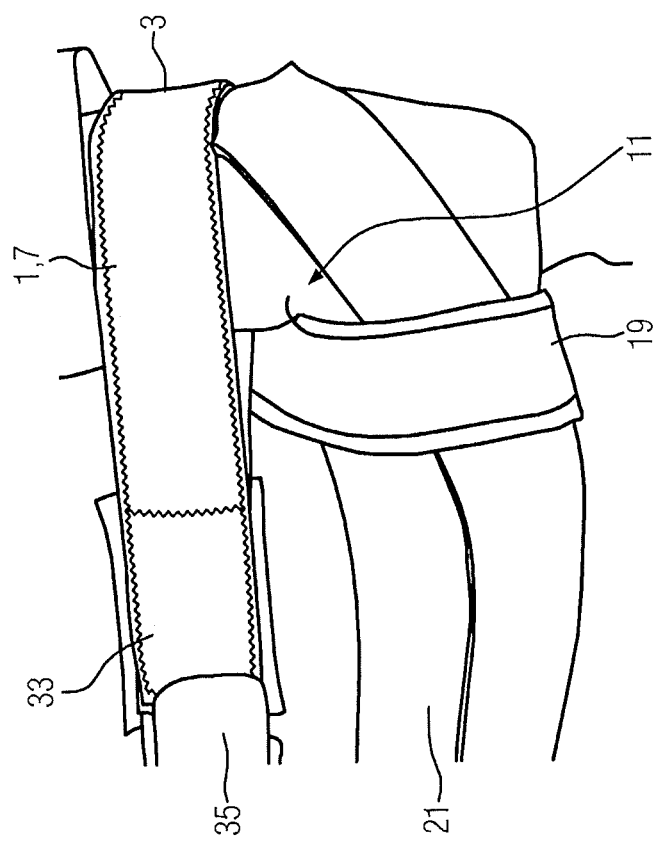
FIG. 5 shows the anterior part in the region of the arm section of the first exemplary embodiment in the fitted and closed state.

As shown in particular in FIGS. 2, 3 and 5, there is provided in this exemplary embodiment a shoulder strap 17 whose first end 19 forms a second strap section, wherein the first end 19 loops around the arm section 11 of the arm 13 of the patient. Here, the first end 19 lies against the lower arm 21 adjacent to the elbow. The shoulder strap 19 extends posteriorly and diagonally over the back of the patient to the contralateral shoulder 23 in relation to the first shoulder joint 15. As shown in FIG. 1, the shoulder strap 17 runs anteriorly from the contralateral shoulder 23 in a vertical direction to the circular strap 1, and is preferably detachably connected to said circular strap there at a first connecting point.

Figure 6:
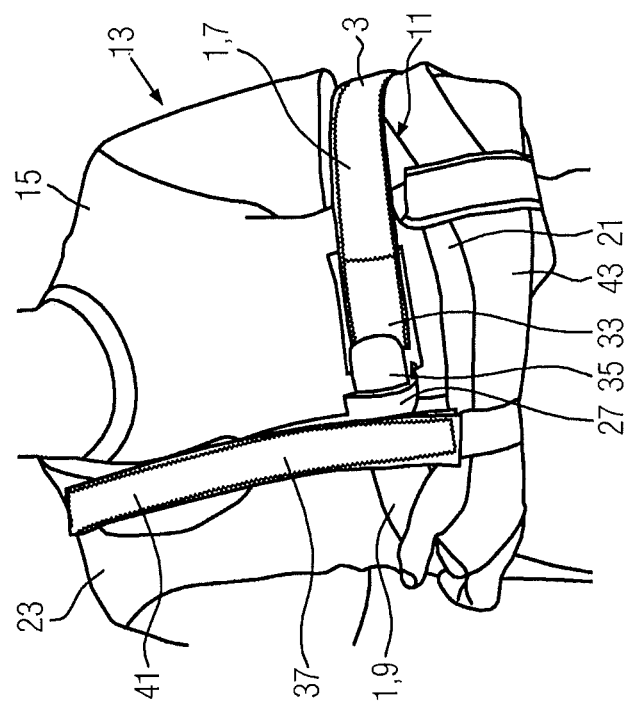
FIG. 6 shows the anterior part of the first exemplary embodiment in the fitted and closed state, with the arm fixed in the flexed state.

As can be seen from FIGS. 1 and 6, a fastener device 27 is provided which, in the closed state of the orthosis, is arranged in the region of a virtual junction point 25 (see FIGS. 1 and 2). The fastener device 27 is connected to the second end 29 of the shoulder strap 17 such that the fastener device 27 can be displaced along the shoulder strap 17. However, said connection is preferably designed such that the shoulder strap 17 cannot simply slide through the fastener device 27; rather, said connection is designed so as to hold the shoulder strap 17 in a predefined position relative to the fastener device 27 in the event of load acting in the profile direction of the shoulder strap 17. In order to displace the first connecting point, said connection must preferably initially be moved into a released position. Furthermore, the fastener device 27 is connected to the posterior section 9 of the circular strap 1, wherein said fastener device is likewise displaceable in the longitudinal direction thereof. For this purpose, the fastener device 27 is equipped with a fixing device, described in more detail below. The second end 29 of the shoulder strap 17 and the circular strap 1 or the posterior section 9 are thus connected to one another by means of the fastener device 27. Furthermore, by virtue of the fact that the fastener device 27 is attached displaceably to the circular strap 1 and to the shoulder strap 17, a first connecting point at which the shoulder strap 17 and the circular strap 1 are connected to one another is displaceable along the circular strap 1 and along the shoulder strap 17.

The fastener device 27 is equipped with a connecting element in the form of an eyelet 31, by means of which the free end 33 of the anterior section 7 can be connected to the fastener device 27 by virtue of a hook 35 on the free end 33 of the anterior section 7 engaging into the eyelet 31. The fastener device 27 is in the closed position when the hook 35 engages into the eyelet 31, and is otherwise in the open position. It can be seen here that the shoulder strap 17 and the posterior section 9 are connected to one another both in the closed position and in the open position.

FIG. 2 also shows that a holding strap 37 is provided, the first end 39 of which is connected to the second end 29 of the shoulder strap 17, wherein, in this preferred exemplary embodiment, the shoulder strap 17 and the holding strap 37 are formed in one piece, such that the shoulder strap 17 merges into the holding strap 37 at the fastener device 27. The second end 41 of the holding strap 37 may be detachably connected to the shoulder strap 17, such that the holding strap 37 forms a loop in which the wrist of the lower arm 21 extending from the first shoulder joint 15 can be received (see FIG. 6).

Finally, it emerges in particular from FIGS. 1 and 6 that the orthosis has a lower arm support 43 which receives the lower arm 21 of the arm 13 extending from the first shoulder joint 15 and which is connected, in the arm section 11 of said arm 13, to the circular strap 1 and to the shoulder strap 17. The lower arm support 43 is however not necessary for the functioning of the orthosis.

The fixing device, which is attached to the fastener device 27 and which is not illustrated in detail, is provided for fixing the position of the first connecting point, at which the shoulder strap 17 and the posterior section 9 are connected to one another, along the posterior section 9. The fixing device is designed such that the first connecting point can be displaced toward the second end 5 by pulling on the posterior section end 45 remote from the second end 5 of the circular strap 1 or of the posterior section 9, whereas a movement of the first connecting point towards the posterior section end 45 as a result of a pulling action on the second end 5 is blocked. This means that the posterior section 9 can be pulled through the fastener device 27 by pulling on the end 45 thereof, whereas a movement of the posterior section 9 in the opposite direction is blocked.

The first exemplary embodiment of an orthosis as described above is fitted as follows.

Firstly, the lower arm 21 is received in the lower arm support 43, and the arm section 11 is received in the ends 3, 19 of the circular strap 1 and of the shoulder strap 17, wherein these then at least partially loop around the arm section 5 either in the upper arm region or in the lower arm region.

Since the second end 29 of the shoulder strap 17 and the posterior section 9 are connected to one another by means of the fastener device 27 even in the open position of the latter, the posterior section 9 and the shoulder strap 17 initially form a loop in which the contralateral shoulder 23 in relation to the first shoulder joint 15 can be received, or the patient must merely hang said loop over the contralateral shoulder 23. This yields the situation shown in FIG. 1.

Subsequently, the fastener device 27 is closed by virtue of the hook 35 on the free end 33 of the anterior section 7 being inserted into the eyelet 31. Finally, the circular strap 1 can then be tightened by pulling on the posterior section end 45, wherein the fastener device 27 is designed, in the manner described above, such that a return movement of the posterior section 9 is not possible. This gives rise to the situation illustrated in FIG. 2, wherein it can be seen in FIG. 3 that the posterior section end 45 can be secured to the posterior section 9.

Finally, the patient can fix the lower arm 21 by virtue of the holding strap 37 being looped around that section of the lower arm support 43 which receives the wrist, wherein then, the second end 41 of the holding strap 37 is secured to the shoulder strap 17 above the fastener device 27 (see FIG. 6).

Accordingly, in the case of the orthosis described above, a first and a second strap section, specifically the first end 3 of the circular strap 1 and the first end 19 of the shoulder strap 17, are provided, which engage on the arm section 11 by at least partially looping around the latter, such that tension in the direction of extent of the strap sections causes the arm section 11 to be acted on with a first and a second force. In the fitted state of the orthosis, in which the arm 13 extending from the injured shoulder joint 15 lies laterally and/or frontally against the body, the first strap section or the first end 3 of the circular strap 1 exerts on the arm section 11 a force which is directed toward the body and which preferably runs substantially parallel to the frontal plane of the patient but which has at least a first component running horizontally and parallel to the frontal plane. In this way, owing to the first strap section, the arm section 11 is pulled against the body, such that the first force component has an adductive effect on the first arm 13. At the same time, the second strap section, that is to say the first end 19 of the shoulder strap 17, exerts on the arm section 11 a second force (F2; see FIG. 4) which has at least a component running horizontally and parallel to the sagittal plane and thus perpendicular to the first component and directed toward the posterior, resulting in a slight retroversion of the arm 13. Owing to this combination of the two force components, the arm 13 is reliably fixed to the body.

Furthermore, the advantage is achieved that the first shoulder joint 15, which is to be immobilized, is immobilized both when the elbow is extended and also when the elbow is flexed.

Furthermore, the fastener device 27 has the great advantage for the patient that, simply by releasing said fastener device, that is to say by transferring said fastener device from the closed position into the open position, the action of both forces on the arm section 11 is eliminated, such that the arm 13 extending from the injured shoulder joint 15 is immediately released. Conversely, the action of both forces can be immediately obtained simply by closing the fastener device 27, without further measures having to be taken by the patient. This simplifies the fitting process considerably.

FIGS. 7 to 11 show a second exemplary embodiment of an orthosis according to the invention in different stages of the fitting process. This example likewise has a circular strap 101 which has a first and a second end 103, 105. The circular strap 101 likewise comprises an anterior section 107, which extends from the first end 103 and runs anteriorly over the patient, and a posterior section 109, which runs posteriorly and horizontally around the patient from the second end 105.

In this exemplary embodiment, the first end 103 of the circular strap 101 forms a first strap section which loops around the arm section 11 of the arm 13 of the patient, wherein this takes place, adjacent to the elbow, on the upper arm. The second end 105 of the circular strap 101 likewise loops around the arm section 11, wherein this however takes place on the lower arm 21.

Furthermore, this exemplary embodiment has a shoulder strap 117, which in this exemplary embodiment is not engaged on the arm section 11. Rather, the first end 119 of said shoulder strap is connected to the posterior section 109 of the circular strap 101 (see FIG. 9). The connection between the first end 119 of the shoulder strap 117 and the circular strap 101 is in this case configured such that the first end 119 loops around the circular strap 101, such that the second connecting point, at which the first end 119 is connected to the circular strap 101 or to the posterior section 109, is preferably displaceable along the circular strap 101 or along the posterior section 109. In this way, the position of the first end 119 of the shoulder strap 117 can be adjusted. The shoulder strap 117 extends over the contralateral shoulder 21 in relation to the first shoulder joint 9, which is to be immobilized, to the virtual junction point 25.

In this exemplary embodiment, too, the anterior section 107 runs anteriorly over the body of the patient to the virtual junction point 25, wherein the free end 133 of the anterior section 107 is equipped with a hook-and-loop fastener element 135. Even though hook-and-loop fastener elements are described hereinafter with regard to the connection of anterior section 107 and posterior section 109 or fastener device 127, it is also possible instead of this to use other means for producing a detachable connection.

Figure 8:
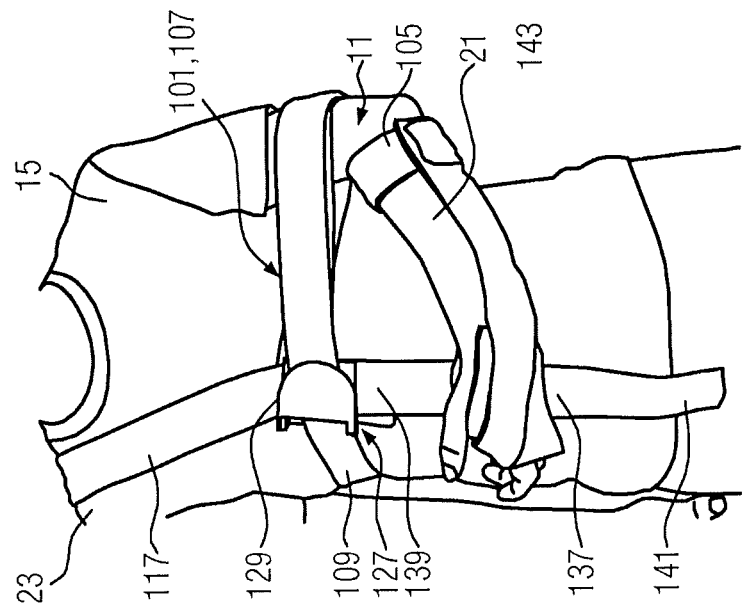
FIG. 8 shows the anterior part of the second exemplary embodiment in the fitted and closed state, with the arm not fixed.
Figure 7:
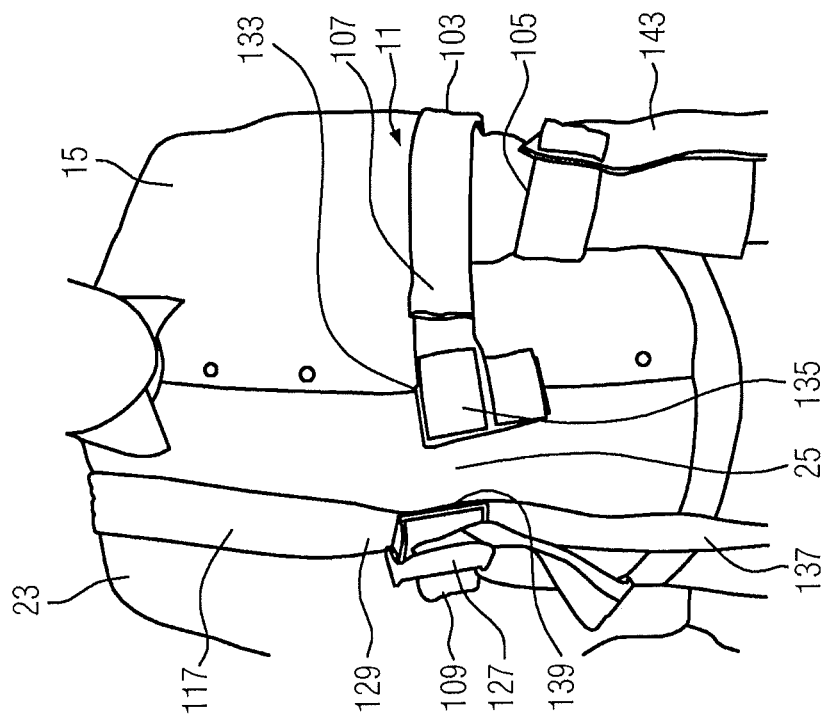
FIG. 7 shows the anterior part of a second exemplary embodiment of an orthosis in the fitted and non-closed state.
Figure 10:
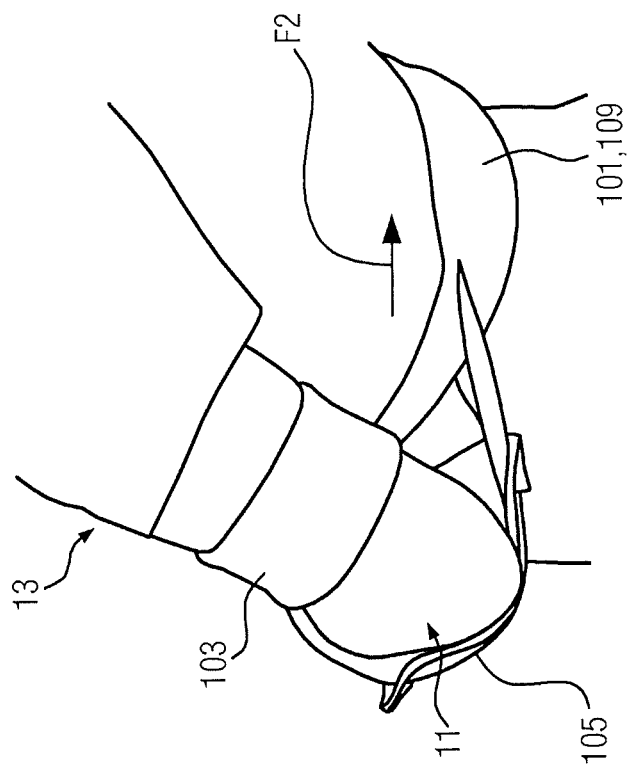
FIG. 10 shows the lateral part of the second exemplary embodiment in the fitted state.
Figure 9:
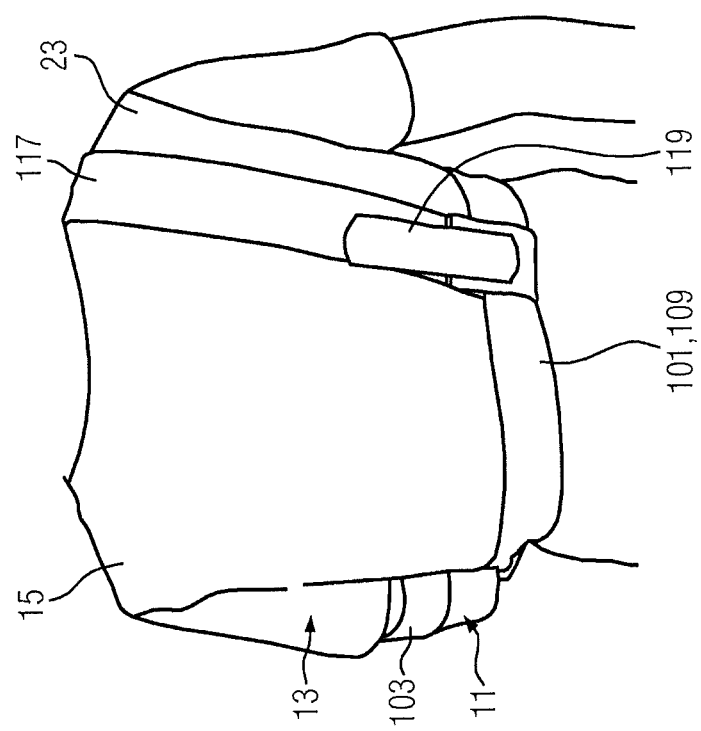
FIG. 9 shows the posterior part of the second exemplary embodiment in the fitted and closed state.

As emerges from FIGS. 8 and 10, this exemplary embodiment also has a fastener device 127 which, in the closed state of the orthosis, is situated in the region of the virtual junction point 25 (see FIG. 8). The fastener device 127 is connected to the second end 129 of the shoulder strap 117 such that the fastener device 127 can be displaced along the shoulder strap 117. Here, too, said connection is preferably designed such that the shoulder strap 117 cannot simply slide through the fastener device 127. Said connection is rather configured so as to hold the shoulder strap 117 in a predefined position relative to the fastener device 127 in the event of load acting in the profile direction of the shoulder strap 117. In order to displace the first connecting point, said connection must preferably initially be moved into a released position. Furthermore, the fastener device 127 is connected to the posterior section 109 of the circular strap 1, wherein said fastener device is likewise displaceable in the longitudinal direction thereof. For this purpose, the fastener device 127 is equipped with a fixing device, described in more detail below. It is thus also the case here that the second end 129 of the shoulder strap 117 and the circular strap 101 or the posterior section 109 are connected to one another by means of the fastener device 127. Furthermore, by virtue of the fact that the fastener device 127 is attached displaceably to the circular strap 101 and to the shoulder strap 117, a first connecting point at which the shoulder strap 117 and the circular strap 101 or the posterior section 109 are connected to one another is displaceable along the circular strap 101 or the posterior section 109 and along the shoulder strap 117.

In this exemplary embodiment, the fastener device 127 is equipped with a connecting element in the form of a hook-and-loop fastener element 138 which can be detachably connected to the hook-and-loop fastener element 135 on the free end 133 of the anterior section 107, such that the fastener device 127 also has a closed position, in which the free end 133 of the anterior section 107 and the posterior section 109 are connected to one another, and an open position, in which the free end 133 of the anterior section 107 and the posterior section 109 are detached from one another.

FIG. 8 in particular shows that, here, too, a holding device for the lower arm is provided in the form of a holding strap 137, the first end 139 of which is connected to the second end 129 of the shoulder strap 117, in this case by virtue of the shoulder strap 117 and the holding strap 137 being formed in one piece, such that the shoulder strap 117 merges into the holding strap 137 at the fastener device 127. The second end 141 of the holding strap 137 can be detachably connected to the shoulder strap 117 by means of a hook-and-loop connection, such that, by means of the holding strap 137, a loop can be formed in which the wrist of the lower arm 21 extending from the first shoulder joint 15 can be received (see FIG. 11).

Figure 11:
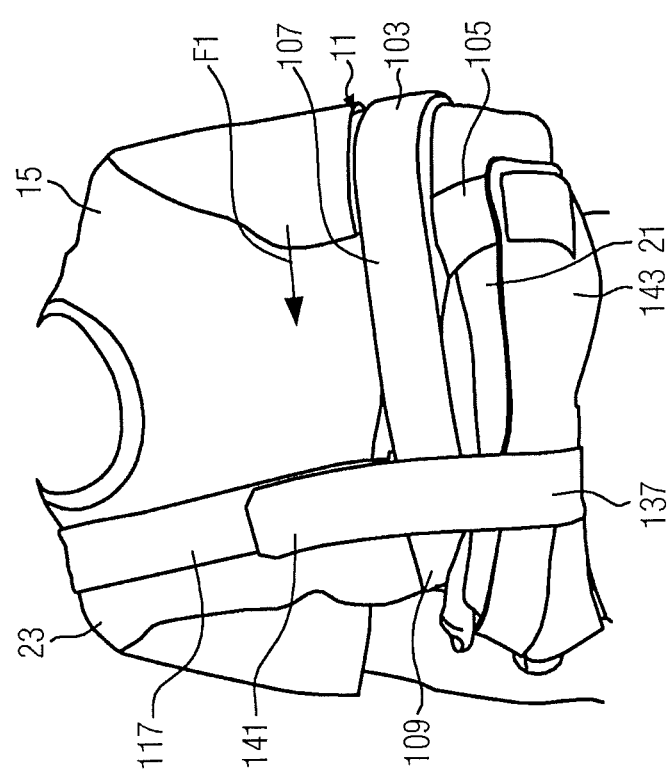
FIG. 11 shows the anterior part of the second exemplary embodiment in the fitted and closed state, with the arm flexed but not fixed.

Finally, it can be seen in particular from FIGS. 8 and 11 that, in this exemplary embodiment of an orthosis according to the invention, too, a lower arm support 143 is provided, wherein such a support is however not necessarily required. The lower arm support 143 receives the lower arm 21 of the arm 13 and is connected, in the arm section 11 of said arm 13, to the second end 105 of the circular strap 101.

The fixing device, which is attached to the fastener device 127 and which is not illustrated in detail here either, is provided for fixing the position of the first connecting point, at which the shoulder strap 117 and the posterior section 109 are connected to one another, along the posterior section 109. The fixing device is designed such that it can assume a locked position and a released position. In the locked position, the first connecting point can be displaced toward the second end 105 by pulling on the posterior section end 145 remote from the second end 105 of the circular strap 101 or of the posterior section 109, whereas a movement of the first connecting point toward the posterior section end 145 as a result of a pulling action on the second end 105 thereof is blocked. In other words, the posterior section 109 can, by pulling on its end 145, be pulled through the fastener device 127, whereas a movement of the posterior section 109 in the opposite direction is blocked by the fixing device when the latter is in the locked position. By contrast, in the released position, a movement of the first connecting point toward the posterior section end 145 is possible by pulling on the second end 105 of the circular strap 101 or of the posterior section 109. This means that, in the released position, the posterior section 109 can be pulled through the fastener device 127 such that the end 145 of said posterior section moves toward the fastener device 127.

The second exemplary embodiment of an orthosis according to the invention, as described above, is fitted in the following way.

Firstly, the patient places the lower arm 21 into the lower arm support 143, and the arm section 11 is received in the loop-shaped first ends 103, 105 of the circular strap 101, wherein the first end 103 of the circular strap 101 loops around the arm section 11 in the upper arm region, and the second end 105 loops around the lower arm region.

Since the first end 119 of the shoulder strap 117 is connected to the posterior section 109 of the circular strap 101 and the second end 129 of the shoulder strap 15 and the circular strap 1 are likewise connected to one another by means of the fastener device 127 regardless of the position thereof, the circular strap 101 and the shoulder strap 117 together form a loop in which the contralateral shoulder 23 in relation to the first shoulder joint 15 can be received, or the patient must merely hang said loop over the contralateral shoulder 23. This results in the situation illustrated in FIG. 7.

Subsequently, the fastener device 127 is moved into the closed position in which the free end 133 of the anterior section 107 is fixed by virtue of the hook-and-loop fastener elements 135, 138 being connected. Finally, the circular strap 101 can then be tightened by pulling on the posterior section end 145, wherein the fixing device of the fastener device 127 is in the locked position, such that a return movement of the circular strap 101 is not possible. The tensioning can thus be performed using only the arm extending from the contralateral shoulder 23. This results in the situation illustrated in FIGS. 8 and 9.

Finally, the patient can fix the lower arm 21 to the body by virtue of the holding strap 137 being looped around that section of the lower arm support 143 which receives the wrist, wherein the second end 141 of the holding strap 137 is then secured to the shoulder strap 117 above the fastener device 127 (see FIG. 11).

In this second exemplary embodiment, too, the circular strap 1 can be tensioned in a simple manner, wherein the arm 13 extending from the first shoulder joint 15 is securely fixed. Here, too, it is the case that two strap sections, specifically the first and the second end 103, 105 of the circular strap 101, exert two forces on the arm section 11 such that the latter is reliably fixed. In the fitted state of the orthosis, the first end 103 of the circular strap 1 exerts on the arm section 11 a force which is directed toward the body and which preferably runs substantially horizontally and parallel to the frontal plane of the patient, but has at least a first component running horizontally and parallel to the frontal plane. In addition, the second end 105 of the circular strap 101 exerts on the arm section 11 a second force which has at least a component running parallel to the sagittal plane and thus perpendicular to the first component and directed toward the posterior. Furthermore, it is also the case here that the first shoulder joint 15 is fixed both when the elbow of the arm 13 is extended and also when said elbow is flexed.

Finally, it is also the case here that the fastener device 127 is advantageously arranged such that, simply by transferring said fastener device from the closed position into the open position, that is to say by releasing the hook-and-loop fastener elements 135, 138, the action of both forces on the arm section 11 is eliminated, such that the arm 13 extending from the injured shoulder joint 15 is immediately released.

FIGS. 12 to 15 firstly show the fastener of a third exemplary embodiment of an orthosis according to the invention for immobilizing a shoulder joint, without said fastener being connected to the strap arrangement of the orthosis, whereas FIGS. 16 to 24 show the third exemplary embodiment itself.

Figure 12:
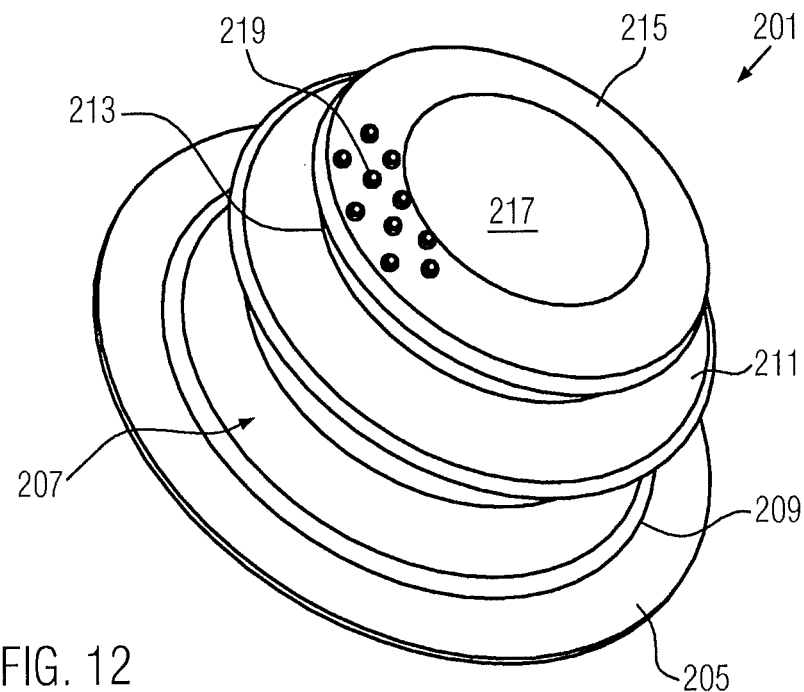
FIG. 12 shows the first fastener part of the fastener of the third exemplary embodiment in a perspective view.
Figure 14:
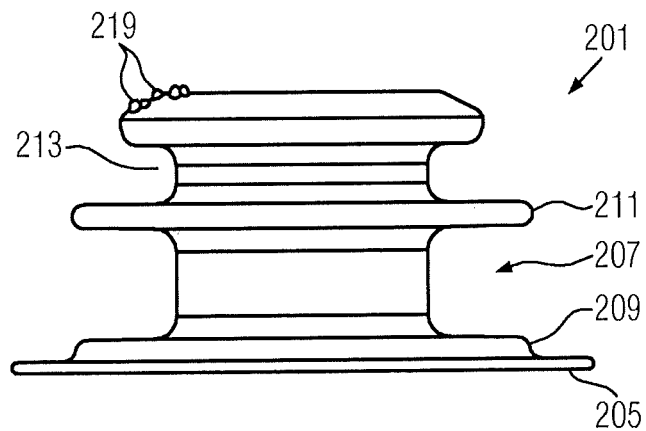
FIG. 14 shows the first fastener part of the fastener of the third exemplary embodiment in a side view.
Figure 15:
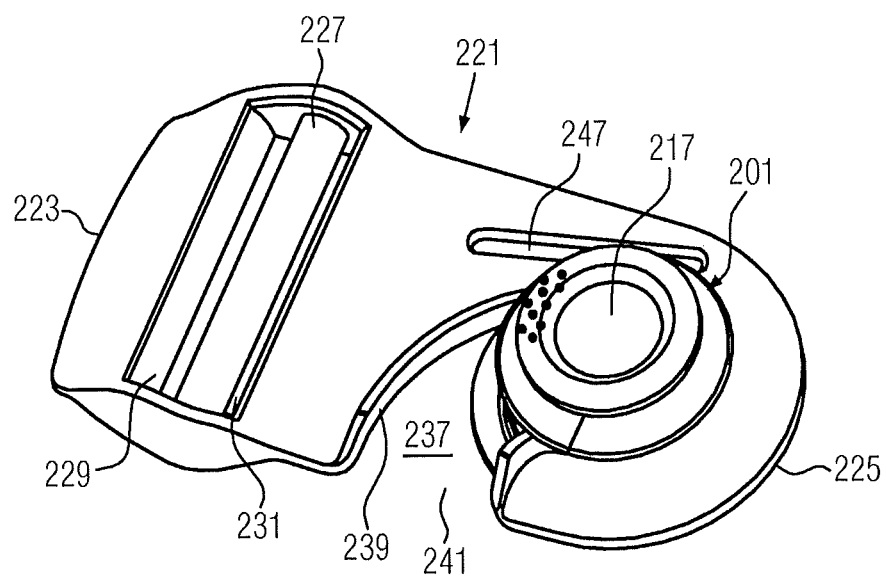
FIG. 15 is a perspective illustration of the fastener of the third exemplary embodiment in the closed state.

The first fastener part 201, illustrated in FIGS. 12 and 14, of the exemplary embodiment comprises a stud 203 and has a connecting device in the form of a flange 205, by way of which connecting device said first fastener part can be connected to an end of a strap of a strap arrangement, for example by welding, adhesive bonding or sewing. The stud 203 of the first fastener part 201 is provided with a first section 207 which extends between a first projection 209 and a second section in the form of a second projection 211. The first section 207 is thus arranged close to the connecting device, which is in the form of a flange 205, and the second section or the second projection 211 adjoins the first section 207 at that end of the latter which is situated opposite the connecting device or the flange 205. The diameter and thus the dimensions of the projections 209, 211 perpendicular to the direction of extent of the stud 203 are greater than the diameter or the dimensions of the cylindrical first section 207.

On that side of the first section 207 which faces away from the flange 205, there is provided on the stud 203 an undercut 213 which serves for receiving a cutout in a strap end. The undercut 213 on the free end of the stud 203 thus constitutes a further connecting device by means of which, for example, a further strap can be detachably connected to the first fastener part 201. As can finally be seen from FIG. 1, the free end 215 of the stud 203, which faces away from the flange 205, has a depression 217 which extends in an axial direction of the stud 203 and which is dimensioned such that it can accommodate the finger of a patient, and the first connecting part 201 can thus be held in position when the fastener is being fastened. Here, in order that the first fastener part 201 can be held with additional security, a multiplicity of projections 219 are provided on the end surface of the free end 215 around the depression 217, which projections additionally prevent the fingers of the patient from slipping.

Figure 13:
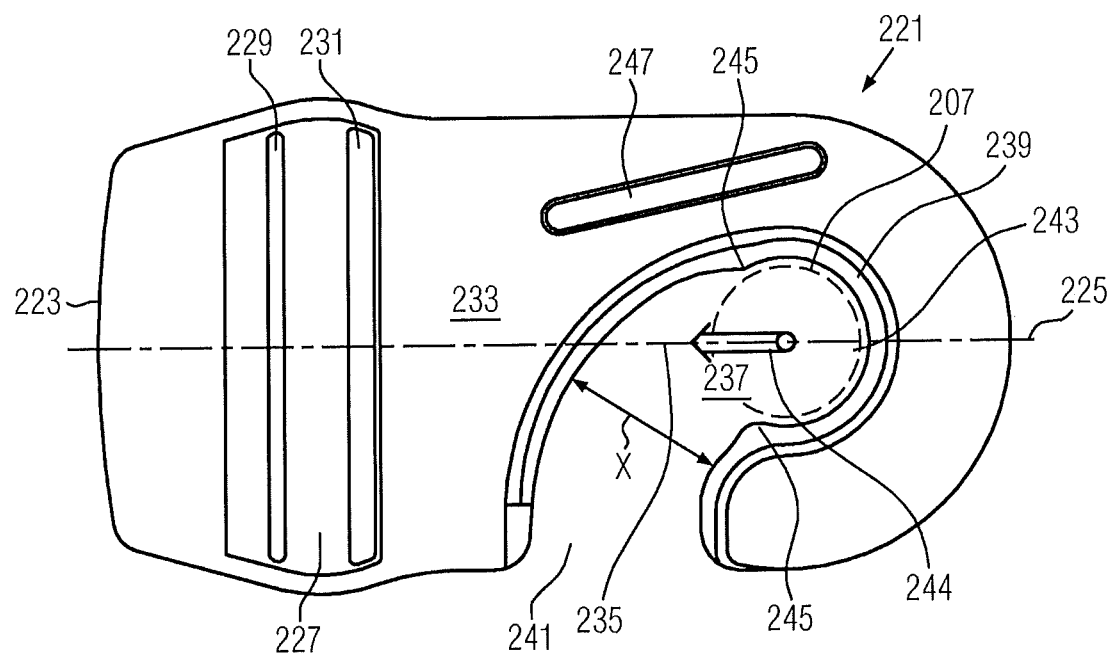
FIG. 13 shows the second fastener part of the fastener of the third exemplary embodiment in a plan view.

FIG. 13 illustrates the second fastener part 221 in a plan view. The second fastener part 221 has an attachment end 223 and a coupling end 225. In the region of the attachment end 223 there is provided a first connecting device for a strap end, which first connecting device is, in this exemplary embodiment, designed such that a first slot 229 and a second slot 231 extend parallel to a web 227, wherein the second slot 231 is further remote than the first slot 229 from the attachment end 223. To connect a strap end to the first connecting device, said strap end is led, proceeding from the attachment end 223 along one side of the second connecting part 221 and firstly through the second slot 231, then around the web 227, and finally through the first slot 229 and back to the attachment end 223. By virtue of the first slot 229 being delimited with a sharp edge on the side facing away from the web 227, a strap end can thus be connected to the first connecting device in self-fixing fashion, wherein the position of the strap end relative to the second connecting part 221 is adjustable.

The second fastener part 221 furthermore has a planar section 233 which extends way from the attachment end 223, or the first connecting device 227, 229, 231, to the coupling end 225. The planar section 233 in this case extends along a connecting line 235 between the attachment end 223 and the coupling end 225. In the planar section 233 there is formed, as a cutout, a guide track 237 which is surrounded by an abutment section formed web 239 with constant thickness, such that the planar section 233 is formed with a uniform thickness in the region around the guide track 237. Owing to the web 239, the thickness of the planar section 233 in the region of the guide track 237 corresponds to the distance between the first and second projections 209, 211, or the length of the first section 207 in the axial direction of the stud 203, such that the first fastener part 201, when it is situated in the guide track 237, cannot move in the axial direction of the stud 203 relative to the second fastener part 221. Furthermore, the guide track 237 extends in a fastener plane defined by the planar section 233.

The guide track 237 has a uniformly curved profile and extends from an entry opening 241 to a guide track end 243, wherein in this preferred exemplary embodiment, the entry opening 241 is formed on the edge of the planar section 233 and thus of the second fastener part 221. The entry opening 241 is, regardless of its position in the second fastener part 221, formed such that the first fastener part 201 can be inserted through it into the guide track 237. If the entry opening 241 is formed in the edge, the second fastener part 221 can be simply pushed onto the first section 209 of the stud 203. It is however also conceivable for the entry opening to be in the form of a bore with enlarged dimensions in relation to the guide track end 243, such that the second section or the second projection 211 can be initially pushed through the bore before the first section 207 is then displaced in the guide track 237, wherein the edge of the guide track 237 then bears against the first section 207.

The guide track 237 is thus designed such that every possible movement 244 of the stud 203 out of its position in the guide track end 243 runs such that at least the projection of said movement 244 onto the connecting line 235 points toward the attachment end 223, wherein the position of the first section 207 of the stud 203 in the guide track end 243 is indicated by dashed lines in FIG. 13. In the exemplary embodiment shown here, the movement 244 of the stud 203 itself runs parallel to the connecting line 235. It is however also conceivable for the movement to run obliquely with respect to the connecting line. In any case, the guide track 237 is however designed, at the guide track end 243, such that either the movement has at least a component pointing toward the attachment end 223, or the movement runs perpendicular to the connecting line 235.

The movement path away from the guide track end 243 thus does not have any component which both runs parallel to the connecting line 235 and is directed toward the coupling end 225. In other words, the stud 203, if it is to be moved from the guide track end 243 to the entry opening 241, must imperatively move away from the coupling end 225. To perform such a movement, it is necessary, if the fastener is integrated into a strap arrangement of an orthosis, for the first fastener part 201 to be moved counter to the force exerted on the fastener by the preload of the strap arrangement. This has the effect that the fastener is self-locking. It is however also conceivable for the movement of the stud 203 out of the guide track end 243 to run perpendicular to the connecting line 235 between the attachment end 223 and the coupling end 225. Then, if the fastener is under tension, at least friction forces act which prevent a movement of the stud 203 in the guide track 237.

As can also be seen from FIG. 13, the connecting line 235 also runs from the attachment end 223 with the first connecting device to the coupling end 225 through the guide track end 243, wherein the connecting line 235 also runs through the central axis of the stud 203, or of the first section 207, when this is situated in the guide track end 243.

The width X of the guide track 237, and thus the dimension thereof perpendicular to the tangent to the profile thereof, corresponds to the diameter of the first section 207 of the first fastener part 201, with the exception of a region between detent projections 245, in which the width is reduced. It may however also conceivably be provided that the width of the guide track 237 does not correspond over the entire length thereof to the dimensions of the first section 207, but is formed so as to be considerably larger at a distance from the guide track end 243. In any case, it is however necessary for the dimensions of the second section or of the second projection 209 perpendicular to the direction of extent of the stud 203 to be greater than the dimension of the guide track 237 at the guide track end 243, such that the second section 209 restricts a movement of the stud 203 relative to the second fastener part 221 perpendicular to the fastener plane. Where dimensions are referred to in this connection as corresponding, this is to be understood to mean that the first section 207 and the edge of the guide track 237 at the guide track end 243 should not bear against one another so tightly that a displacement of the stud 203 relative to the second fastener part 221 is no longer possible.

The detent projections 245 serve for locking the first fastener part 201 in a position in which said first fastener part is situated at the guide track end 243. As a result, it is necessary in this exemplary embodiment for the first fastener part 201 with the stud 203 to be moved past the projections 245, wherein said projections must be moved out of the guide track 237 counter to an elastic opposing force arising from the elasticity of the planar section 233.

By virtue of the fact that the stud 203 has a circular cross section in the region of the first section 207 and the diameter corresponds to the width X of the guide track, the first fastener part 201 can be pivoted relative to the second fastener part 221.

As can furthermore be seen from FIG. 13, the guide track 237 is designed such that it can receive the first section 207 of the stud 203 and guide it between the entry opening 241 and the guide track end 243. It can also be seen that the entry opening 241, which is formed at the edge of the planar section 233, is arranged such that the projection thereof onto the connecting line 235 is situated further remote from the coupling end 225 than the projection of the guide track end 243 onto the connecting line 235. Thus, if the fastener is integrated into a strap arrangement, a force acts on the first fastener part 201 even at the entry opening 241.

Finally, in the planar section 233 of the second connecting part, there is formed, in the form of a further slot 247, a second connecting device for a strap end, such that the second fastener part 221 can be connected to a second strap end that is led through the further slot 247. Here, the further slot 247 is on one side of the connecting line 235.

As can also be seen from FIG. 13, the entry opening 241 of the guide track 237 is arranged on a first side of the connecting line 235, whereas the second connecting device in the form of the further slot 247 is arranged on an opposite, second side.

If it is sought to connect the fastener parts 201, 221 of this exemplary embodiment to one another, and said fastener parts are each connected to strap ends of a strap arrangement, the second connecting part 221 must initially be moved toward the first fastener part 201, counter to the restoring forces generated by the strap arrangement, to such an extent that the stud 203 can be moved laterally through the entry opening 241 into the guide track 237 in the planar section 233. Subsequently, the stud 203 moves, in this exemplary embodiment owing to the uniform direction of curvature, along the guide track 237, and must be moved, if appropriate by being pushed, past the projections 245 until it reaches the guide track end 243. As that position is the point of the guide track 237 closest to the coupling end 225, the stud is held in said position owing to the restoring forces.

Figure 16:
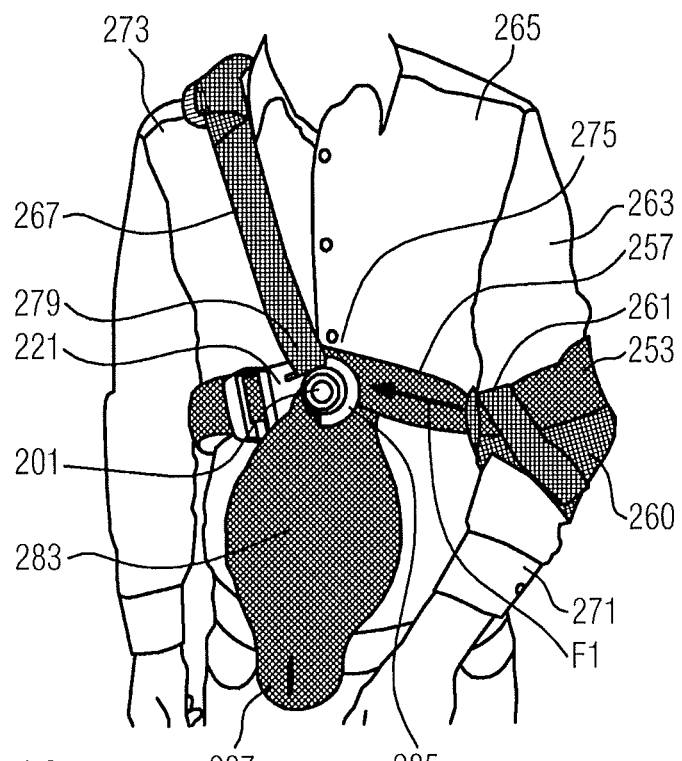
FIG. 16 shows the anterior part of the third exemplary embodiment of a shoulder orthosis, with the orthosis not fully closed.
Figure 17:
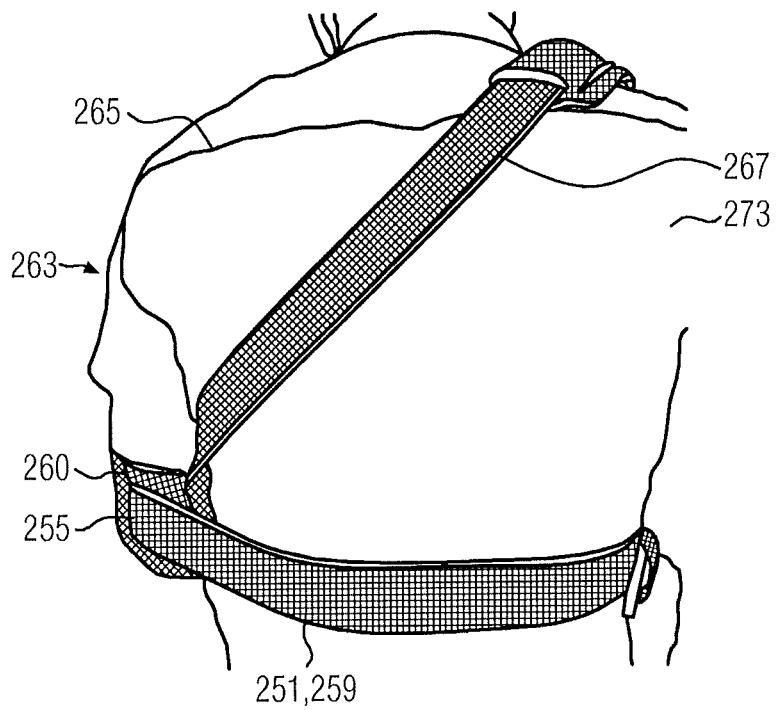
FIG. 17 shows the posterior part of the orthosis from FIG. 16.

As can be seen from FIGS. 16 to 24, the third exemplary embodiment of an orthosis in which the above-described, independently inventive fastener can be integrated is provided for immobilizing a shoulder joint, and has a strap arrangement with a circular strap 251 which has a first and a second end 253, 255 (see FIGS. 16 and 17).

The circular strap 251 is made up of an anterior section 257, which extends from the first end 253 and runs anteriorly over the patient, and a posterior section 259, which runs posteriorly and horizontally around the patient from the second end 255. Here, in this exemplary embodiment, the first and the second end 253, 255 of the circular strap 251 are connected to one another by being fastened adjacently to one another to a receptacle 260 for the elbow, as shown in particular in FIG. 24. In this exemplary embodiment, the first end 253 of the circular strap 251 forms, with the receptacle 260, a first strap section which partially loops around an arm section 261 of that arm 263 of the patient which extends from the first shoulder joint 265, which is to be immobilized.

Here, in the context of the present invention, the expression "arm section" is to be understood to mean that region of the arm 263 extending from the injured first shoulder joint 265 which encompasses the elbow itself and the regions adjacent thereto.

Figure 18:
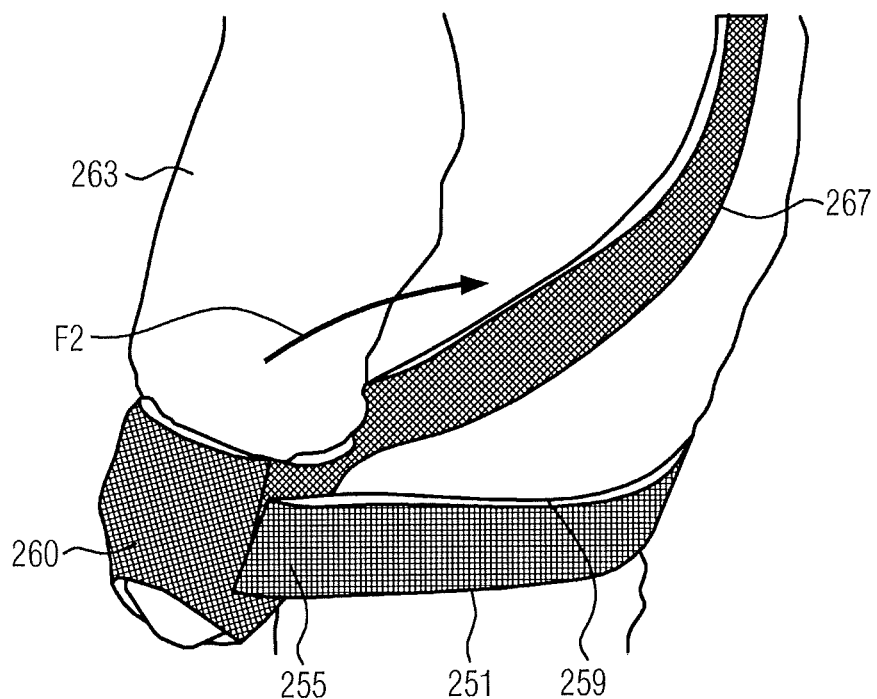
FIG. 18 shows the lateral part of the orthosis from FIGS. 16 and 17.
Figure 19:
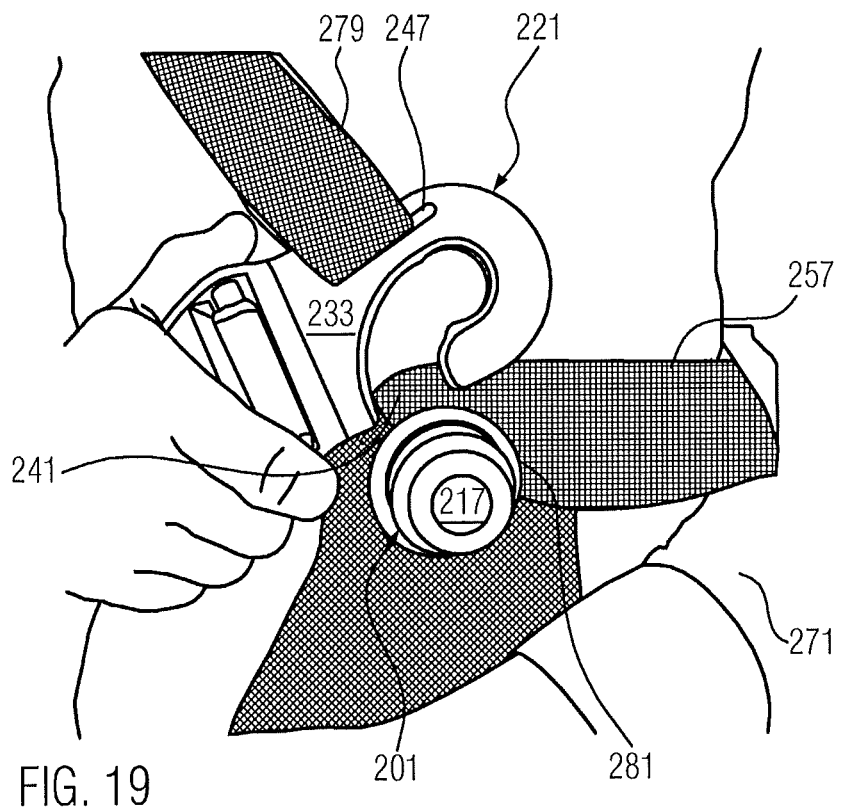
FIG. 19 shows the orthosis from FIGS. 16 to 18 with the fastener in its open position, in detail.
Figure 20:
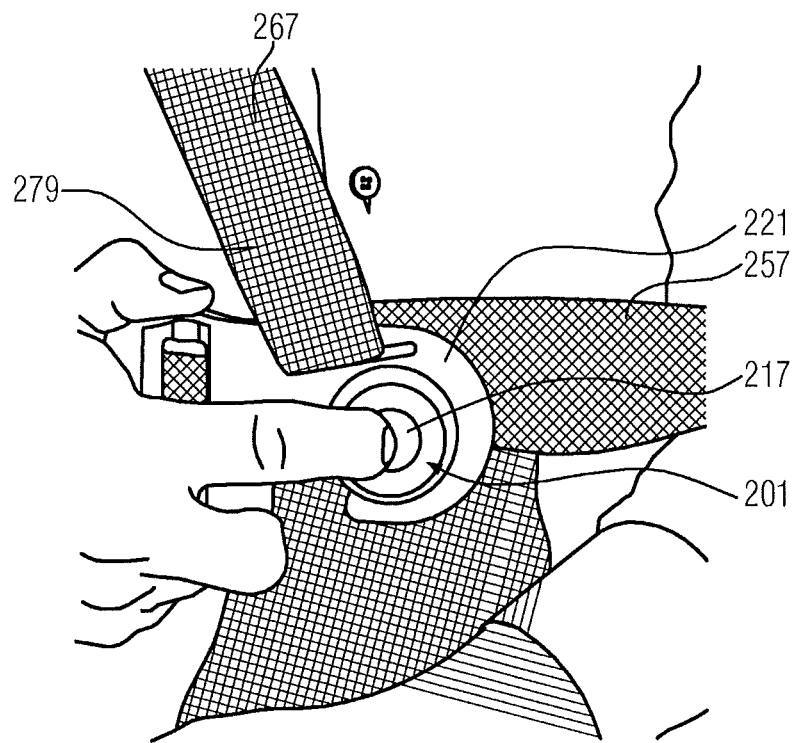
FIG. 20 shows the orthosis from FIGS. 16 to 18 with the fastener fastened, in detail.
Figure 21:
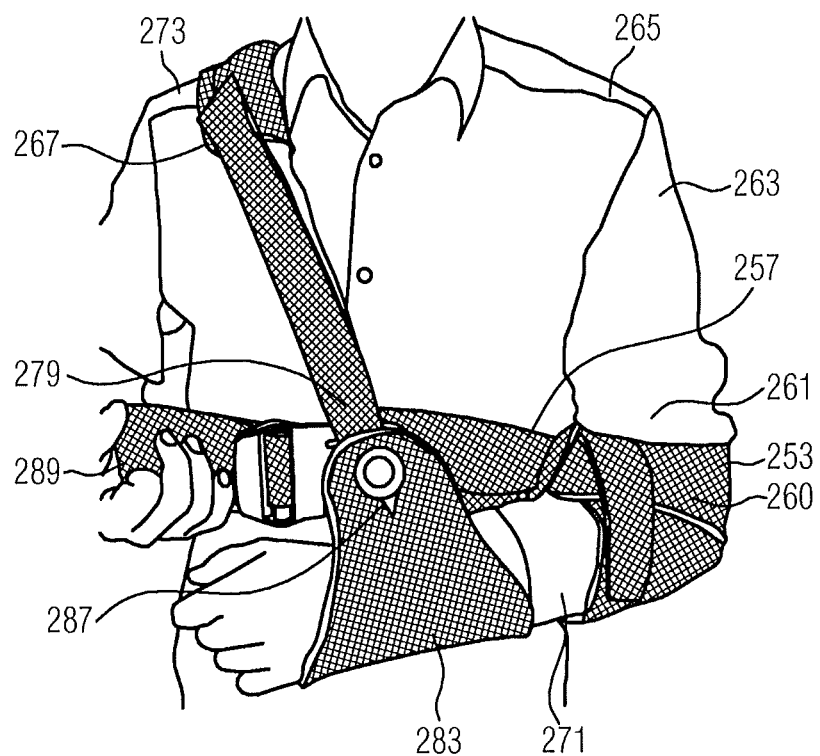
FIG. 21 shows the anterior part of the orthosis from FIGS. 16 to 18 in the fully fastened and fitted state.

It also emerges from FIGS. 16, 17 and 18 that, in the case of this orthosis, a shoulder strap 267 is provided whose first end 269 forms a second strap section, wherein the first end 269 is connected to the receptacle 260 and thus loops around the arm section 261 of the arm 263 of the patient likewise by way of said receptacle. Here, the first end 269 merges into the receptacle 260 at the lower arm 271 adjacent to the elbow. The shoulder strap 269 extends posteriorly and diagonally over the back of the patient to the contralateral shoulder 273 in relation to the first shoulder joint 265. As shown by FIGS. 16 and 21, the shoulder strap 267 runs from the contralateral shoulder 273 anteriorly in a vertical direction to the circular strap 251, and is connected there to said circular strap 251 at a first connecting point by means of the fastener parts 201, 221.

As can also be seen from FIGS. 16 to 24, the fastener with the fastener parts 201, 221 is, in the closed state of the orthosis, arranged in the region of a virtual junction point 275 (see FIG. 16).

Here, the second fastener part 221 is connected to the second end 279 of the shoulder strap 267 in such a way that the second end 279 can be pulled through the further slot 247 and the second fastener part 221 can thus be displaced along the shoulder strap 267. In order to displace the second end 279 of the shoulder strap 267, a hook-and-loop connection must firstly be opened, and the second end 279 can then be pulled to a greater or lesser extent through the further slot 247. Furthermore, the second fastener part 221 is connected to the posterior section 259 of the circular strap 251, wherein the second fastener part 221 is likewise displaceable in the longitudinal direction of said posterior section. For this purpose, the posterior section 259 is, in the manner already described, guided through the first and second slots 29, 231 and around the web 227.

The second end 279 of the shoulder strap 267 and the circular strap 251 or the posterior section 259 thereof are thus connected to one another by means of the second fastener part 221. Furthermore, by virtue of the second fastener part 221 being attached displaceably to the circular strap 251 and to the shoulder strap 267, a first connecting point, at which the shoulder strap 267 and the circular strap 251 are connected to one another, is displaceable along the circular strap 251 and along the shoulder strap 267.

The first fastener part 201 is secured to the free end 281 of the anterior section 257 in such a way that the flange 205 is sewed to the free end 281. It is however also conceivable for the flange 205 to be adhesively bonded or welded to the free end 281.

The first section 207 of the stud 203 can be inserted into the entry opening 241 and moved along the guide track 237 to the guide track end 243 in order to close the fastener formed from the fastener parts 201, 221. It can be seen here that the shoulder strap 267 and the posterior section 259 are connected to one another both in the closed position and in the open position.

Figure 24:
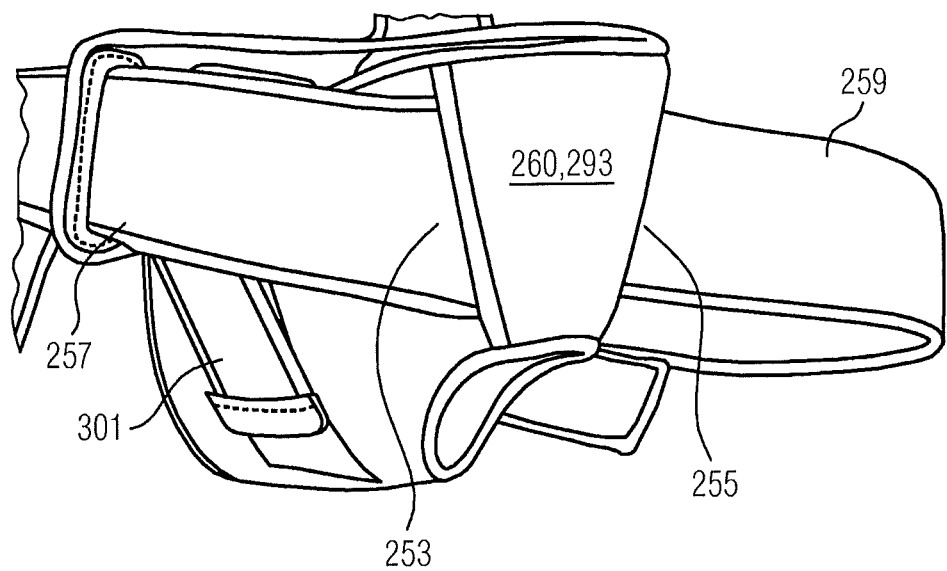
FIG. 24 shows the elbow section of the orthosis from FIGS. 16 to 18 in a side view.

FIGS. 16 and 24 also show that a holding strap 283 is provided, the first end 285 of which is connected to the free end 281 of the anterior section 257. The second end 287 of the holding strap 283 can be detachably connected to the first connecting part 201 by virtue of a cutout 288 in the second end 287 being pressed into the region of the undercut 213 and thus secured to the free end 215 of the stud 203 such that the holding strap 283 forms a loop in which the wrist of the lower arm 271 extending from the first shoulder joint 265 can be received (see FIG. 10). As can also be seen from FIG. 13, reinforcement struts 291 run on the holding strap 283 perpendicular to the direction of extent thereof, which reinforcement struts prevent the holding strap 283 from bending downward, such that a wrist received by the holding strap 283 likewise cannot bend downward.

By means of the two slots 229, 231 provided at the attachment end 223 of the second fastener part 221 and the web 227 arranged in between, a fixing device is provided for the purpose of fixing the position of the first connecting point, at which the shoulder strap 267 and the posterior section 259 are connected to one another, along the posterior section 259. In the case of the construction described above, said fixing device is designed such that the first connecting point can be displaced toward the second end 255 by pulling on the posterior section end 289 that is remote from the second end 255 of the circular strap 251 or of the posterior section 259, whereas a movement of the first connecting point towards the posterior section end 289 as a result of a pulling action on the second end 255 is blocked. This means that the posterior section 259 can, by pulling on its end 289, be pulled through the attachment end 223 through the slots 229, 231, whereas a movement of the posterior section 259 in the opposite direction is blocked.

Figure 22:
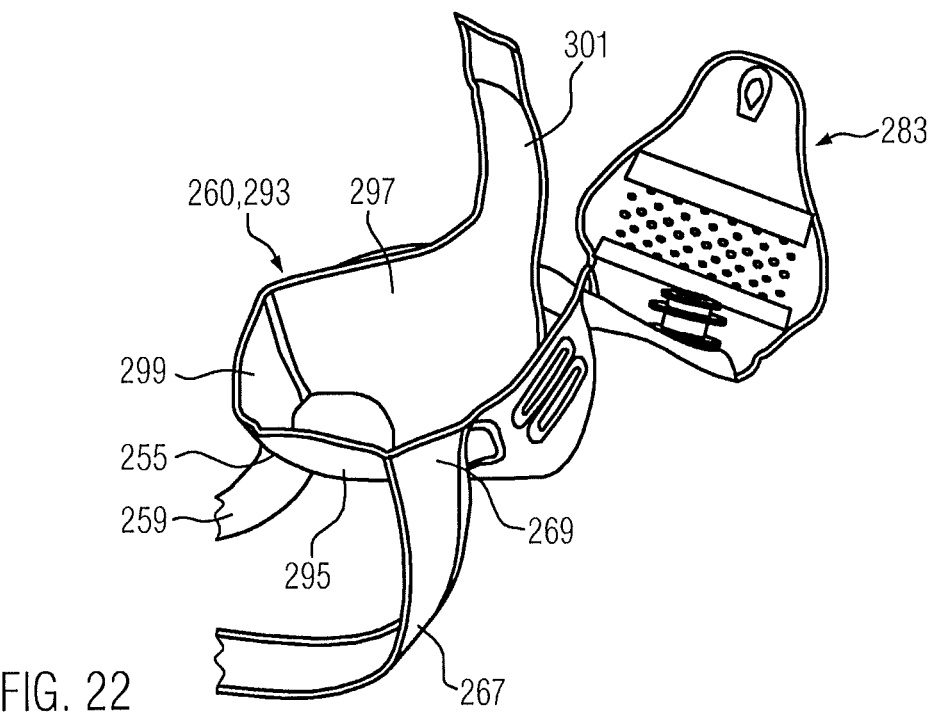
FIG. 22 shows the elbow section of the orthosis from FIGS. 16 to 18 in an open position.
Figure 23:
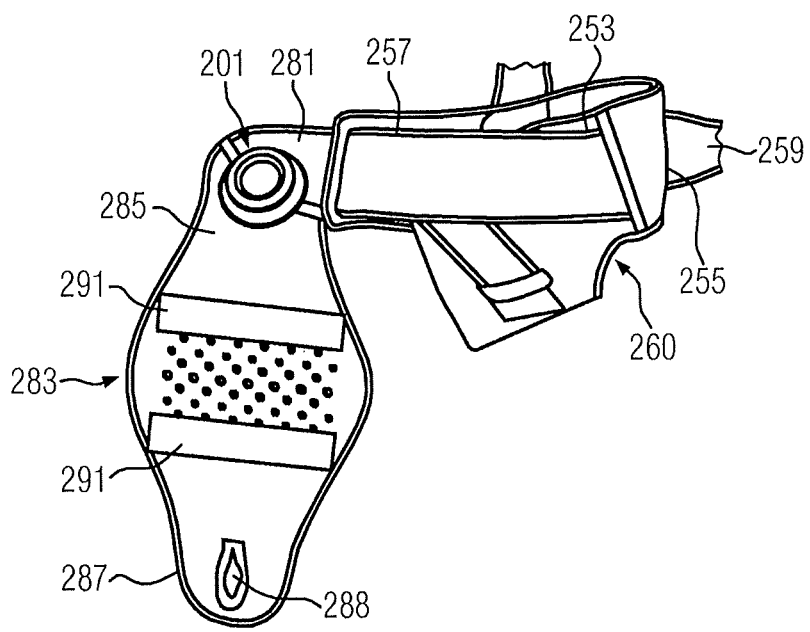
FIG. 23 shows the elbow section of the orthosis from FIGS. 16 to 18 in a closed position.

Finally, as can be seen from FIGS. 22 to 24, the receptacle 260 for the elbow has a device for enabling its width to be adjusted. The receptacle for the elbow has a main body 293 which comprises an inner surface 295, which bears against the body of the patient, an outer surface 297, which is arranged away from the body, and a side surface 299, which bears against the outside of the upper arm. Here, the inner surface 295 and the outer surface 297 are connected to one another at an edge that bears against the lower arm. An adjustment strap 301 is secured to the outer surface 297 at the edge remote from the connection to the inner surface 295, which adjustment strap can be guided through two openings 303 in the inner surface and over the lower arm and in turn detachably fastened to the outer surface 297. By means of the adjustment strap 301, the width of the receptacle 260 can be adapted to patient requirements.

The third exemplary embodiment of an orthosis, as described above, is fitted as follows.

Firstly, the arm section 261 is received in the receptacle 260, which is connected to the ends 253, 269 of the circular strap 251 and of the shoulder strap 267, such that said ends then loop around the arm section 261 by way of the receptacle 260. Here, the adjustment strap 301 is guided over the lower arm of the patient.

Since the second end 279 of the shoulder strap 267 and the posterior section 259 are connected to one another by means of the second fastener part 221 even in the open position of the fastener, the posterior section 259 and the shoulder strap 267 initially form a loop in which the contralateral shoulder 273 in relation to the first shoulder joint 265 can be received, or the patient must merely hang said loop over the contralateral shoulder 273.

Subsequently, the fastener formed from the fastener parts 201, 221 is closed by virtue of the stud 203 being inserted into the entry opening 241 and said stud then being pulled to the guide track end 243 owing to the forces acting on the free end 281 of the anterior section 257, wherein here, however, the detent projections 245 must be pushed out of the guide track 237 counter to the elastic opposing forces acting on them. Here, FIG. 20 in particular shows that the depression 217 in the free end 215 of the stud 203 makes it possible for a fastening of the fastener, with a movement of the stud 203 along the guide track 237, to be performed using only one hand.

When the stud 203 is situated at the guide track end 243, said stud is held at the guide track end 243 owing to the described profile of the guide track 237 and the force acting along the connecting line, which force arises from the preload in the circular strap 251 and in the shoulder strap 267.

Finally, the circular strap 251 can then additionally be tightened by pulling on the posterior section end 289, wherein the second fastener part 221 is designed, in the manner described above, such that a return movement of the posterior section 259 is not possible. This results in the situation illustrated in FIG. 16.

Finally, the patient can fix the lower arm 271 by virtue of the holding strap 283 being looped around the lower arm, wherein the second end 287 of the holding strap 283 is fastened to the stud 203 of the first fastener part 201 (see FIG. 21).

Accordingly, in the case of the orthosis described above, a first and a second strap section, specifically the first end 253 of the circular strap 251 and the first end 269 of the shoulder strap 267, are provided, which engage on the arm section 261 by at least partially looping around the latter with the aid of the receptacle 260, such that tension in the direction of extent of the strap sections causes the arm section 261 to be acted on with a first and a second force. In the fitted state of the orthosis, in which the arm 263 extending from the injured shoulder joint 265 lies laterally and/or frontally against the body, the first strap section or the first end 253 of the circular strap 251 exerts on the arm section 261 a force which is directed toward the body and which preferably runs substantially parallel to the frontal plane of the patient but which has at least a first component running horizontally and parallel to the frontal plane. In this way, owing to the first strap section, the arm section 261 is pulled against the body, such that the first force component has an adductive effect on the first arm 263. At the same time, the second strap section, that is to say the first end 269 of the shoulder strap 267, exerts on the arm section 261 a second force (F2; see FIG. 18) which has at least a component running horizontally and parallel to the sagittal plane and thus perpendicular to the first component and directed toward the posterior, resulting in a slight retroversion of the arm 263. Owing to this combination of the two force components, the arm 263 is reliably fixed to the body.

Furthermore, the advantage is achieved that the first shoulder joint 265, which is to be immobilized, is immobilized both when the elbow is extended and also when the elbow is flexed.

Furthermore, the fastener according to the invention composed of the two fastener parts 201, 221 described in the introduction is associated with the great advantage for the patient that, simply by releasing said fastener, that is to say by transferring said fastener from the closed position into the open position, the action of both forces on the arm section 261 is eliminated, such that the arm 263 extending from the injured shoulder joint 265 is immediately released. Conversely, the action of both forces can be immediately obtained simply by closing the fastener 201, 221, without further measures having to be taken by the patient. This simplifies the fitting process considerably.

In general, the orthosis described above thus comprises a circular strap arrangement 251, 257, 259 which is designed so as to run circularly and horizontally around a patient and which has a first and a second section in the form of the posterior and the anterior section 257, 259 which are provided for being detachably connected to one another at a junction point 275. Furthermore, this orthosis has a shoulder strap arrangement 267 which has a first end 269, connected to the circular strap arrangement 251, 257, 259, and a second end and which is designed to run from posterior to anterior over a shoulder of the patient to the junction point 275. At the junction point 275, the first section of the circular strap arrangement 251, 257, 259, specifically the anterior section 257, is connected to the connecting device of the first fastener part 201, whereas the second section, specifically the posterior section 259, is connected to the connecting device 227, 229, 231 of the second fastener part 221. Finally, the shoulder strap arrangement 267 is connected to the further connecting device 247 of the second fastener part 221.

Here, owing to the construction of the fastener parts 201, 221, it is achieved that the fastener can be closed in a simple manner, if appropriate using only one hand, and remains in said position solely owing to the profile of the guide track 237. In this way, an orthosis equipped with the fastener according to the invention can be fitted and fastened even by a patient with restricted freedom of movement. This does not only apply to the orthosis for fixing a shoulder, as described above; rather, the fastener may in particular also be profitably used with other orthoses which have a circular strap and a shoulder strap arrangement, for example arm abduction cushions or the like.

The foregoing description provides embodiments of the invention by way of example only. It is envisioned that other embodiments may perform similar functions and/or achieve similar results. Any and all such equivalent embodiments and examples are within the spirit and scope of the present invention and are intended to be covered by the appended claims.

We claim:

1. An orthosis for immobilizing a shoulder joint portion of an arm including an upper arm, lower arm, elbow, wrist and hand, of a patient, comprising:
  (a) a shoulder strap for being positioned over a contralateral shoulder and extending diagonally across a back torso of the patient, the shoulder strap having a first end to which is attached an elbow receptacle defining a first arm restraint position, the shoulder strap having a second end adapted to extend down from the contralateral shoulder proximate to a central area of a front torso of the patient, and including a first fastener device positioned on the shoulder strap proximate the second end;
  (b) a torso/arm strap adapted for extending from the elbow receptacle across to the central area of the front torso, and including a second fastener device complementary to the first fastener device for connecting with the first fastener device to define a second arm restraint position proximate the hand and wrist of the patient;

(c) a loop carried by the second end of the shoulder strap and adapted to be looped under and around the hand and wrist area of the arm to support the arm in a laterally-extending position across and adapted to engage at the central area of the front torso of the patient, the first arm restraint position and the second arm restraint position adapted to be located proximate the central area of the front of the torso, and the elbow receptacle and the loop laterally spaced-apart from each other when in place on the arm of the patient; and (d) whereby the first arm restraint position and the second arm restraint position are adapted to be located proximate the central area of the front of the torso and enable the patient to don, adjust and remove the orthosis without assistance.

2. An orthosis according to claim 1, wherein the loop carried by the second end of the shoulder strap includes a relatively wide bottom support portion and a relatively narrow upper attachment portion for interconnecting with the shoulder strap.

3. An orthosis according to claim 2 wherein the relatively wide bottom support portion is laterally spaced apart from the elbow receptacle when in place on the patient.

4. An orthosis according to claim 1, wherein the loop carried by the second end of the shoulder strap is mounted to the shoulder strap that is adapted to pivot in a manner that permits articulation between the shoulder strap and the torso/arm strap.

5. An orthosis according to claim 1, and including a connecting device adapted to interconnect the shoulder strap and the torso/arm strap proximate the front torso, the connecting device being adapted for permitting limited rotational movement of the loop carried by the second end of the shoulder strap and torso/arm strap relative to each other.

6. An orthosis according to claim 1, wherein the loop carried by the second end of the shoulder strap includes an opening adapted for receiving a fastener positioned on one or the other of the shoulder strap or the torso/arm strap proximate a point of intersection between the shoulder strap and the torso/arm strap on the front of the torso of the patient.

7. An orthosis for immobilizing a shoulder joint portion of an arm including an upper arm, lower arm, elbow, wrist and hand, of a patient, and consisting essentially of:

(a) a shoulder strap for being positioned over a contralateral shoulder and extending diagonally across a back torso of the patient, the shoulder strap having a first end to which is attached an elbow receptacle defining a first arm restraint position, the shoulder strap having a second end adapted to extend down from the contralateral shoulder proximate a central area of a front torso of the patient, and including a first fastener device positioned on the shoulder strap proximate the second end;

(b) a torso/arm strap adapted for extending from the elbow receptacle across the front torso, and including a second fastener device complementary to the first fastener device for connecting with the first fastener device to define a second arm restraint position proximate the central area of the front torso and the hand and wrist of the patient;

(c) a loop carried by the second end of the shoulder strap and adapted to be looped under and around the hand and wrist area of the arm to support the arm in a laterally-extending position across and adapted to engage the front torso of the patient, the first arm restraint position and the second arm restraint position being adapted to be located proximate the central area of the front of the torso, and the elbow receptacle and the loop laterally spaced-apart from each other when in place on the arm of the patient; and (d) whereby the first arm restraint position and the second arm restraint position are adapted to be located proximate the central area of the front of the torso and enable the patient to don, adjust and remove the orthosis without assistance.

* * * * *